(12) United States Patent
McCutchen et al.

(10) Patent No.: US 7,214,860 B2
(45) Date of Patent: May 8, 2007

(54) METHODS OF USING NON-PLANT ENCODING NUCLEIC ACIDS

(75) Inventors: Billy F. McCutchen, Clive, IA (US);
Andre R. Abad, W. Des Moines, IA (US); James F. Wong, Johnston, IA (US); Cao Guo Yu, Urbandale, IA (US)

(73) Assignees: Pioneer Hi-Bred International, Inc., Des Moines, IA (US); E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/061,233

(22) Filed: Feb. 18, 2005

(65) Prior Publication Data

US 2005/0198706 A1    Sep. 8, 2005

Related U.S. Application Data

(60) Provisional application No. 60/546,605, filed on Feb. 20, 2004.

(51) Int. Cl.
*C12N 15/82* (2006.01)
*C12N 15/09* (2006.01)
*A01H 5/00* (2006.01)
*A01H 1/00* (2006.01)

(52) U.S. Cl. ............... 800/302; 800/278; 800/279; 800/320; 800/317; 435/69.1; 435/468; 435/469

(58) Field of Classification Search ............... 800/279, 800/278, 298, 295, 306; 536/23.6, 23.2; 435/320.1, 468
See application file for complete search history.

(56) References Cited

U.S. PATENT DOCUMENTS 5,743,477 A    4/1998    Walsh et al.
5,942,659 A    8/1999    Alibert et al.
6,657,046 B1   12/2003   Alibhai et al.

FOREIGN PATENT DOCUMENTS

EP    1 130 100 A1    9/2001

OTHER PUBLICATIONS

Beer et al. Bioch.et Biophys.Acta 1399 (1998) 173-180.*
Berto et al. FEMS Microbiology Letters 180 (1999), pp. 183-189.*
Schmitt, J., et al., "Blocking the Tunnel: Engineering of *Candida rugosa* Lipase Mutants with Short Chain Length Specificity," *Protein Engineering*, 2002, pp. 595-601, vol. 15(7).
Strickland, J., et al., "Inhibition of *Diabrotica* Larval Growth by Patatin, the Lipid Acyl Hydrolase from Potato Tubers," *Plant Physiol.*, 1995, pp. 667-674, vol. 109.

* cited by examiner

*Primary Examiner*—Medina A. Ibrahim
(74) *Attorney, Agent, or Firm*—Alston & Bird LLP

(57) ABSTRACT

Methods of creating and enhancing insect resistance in plants by introducing non-plant lipases into plants are provided. Plants with enhanced insect resistance and seed from plants thereof are provided. DNA sequences encoding insecticidal lipases and insecticidal lipase gene products that are useful in the practice of this invention are also provided. The compositions and methods of the invention may be used in a variety of agricultural systems for controlling pests, including propagating lineages of insect-resistant crops and targeting expression of these insecticidal lipases to plant organs that are particularly susceptible to infestation, such as roots and leaves.

10 Claims, 1 Drawing Sheet

SEQUENCE LISTING

```
<160> NUMBER OF SEQ ID NOS: 8

<210> SEQ ID NO 1
<211> LENGTH: 1650
<212> TYPE: DNA
<213> ORGANISM: Artificial Sequence
<220> FEATURE:
<223> OTHER INFORMATION: Synthetic lipase from C. cylindracea; ctg codon
      substitution for proper expression in plants
<220> FEATURE:
<221> NAME/KEY: CDS
<222> LOCATION: (1)...(1650)

<400> SEQUENCE: 1 atg gag ctc gcc ctc gcc ctc agc ctc atc gcc agc gtc gcc gcc gcc      48
Met Glu Leu Ala Leu Ala Leu Ser Leu Ile Ala Ser Val Ala Ala Ala
 1               5                  10                  15 ccg acc gcc acc ctc gcc aac ggc gac acc atc acc ggc ctc aac gcc      96
Pro Thr Ala Thr Leu Ala Asn Gly Asp Thr Ile Thr Gly Leu Asn Ala
                20                  25                  30 atc atc aac gag gcc ttc ctc ggc atc ccg ttc gcc gag ccg ccg gtc     144
Ile Ile Asn Glu Ala Phe Leu Gly Ile Pro Phe Ala Glu Pro Pro Val
            35                  40                  45 ggc aac ctc cgc ttc aag gac ccg gtc ccg tac agc ggc agc ctc gac     192
Gly Asn Leu Arg Phe Lys Asp Pro Val Pro Tyr Ser Gly Ser Leu Asp
        50                  55                  60 ggc cag aag ttc acc agc tac ggc ccg agc tgc atg cag cag aac ccg     240
Gly Gln Lys Phe Thr Ser Tyr Gly Pro Ser Cys Met Gln Gln Asn Pro
 65                  70                  75                  80 gag ggc acc tac gag gag aac ctc ccg aag gcc gcc ctc gac ctc gtc     288
Glu Gly Thr Tyr Glu Glu Asn Leu Pro Lys Ala Ala Leu Asp Leu Val
                85                  90                  95 atg cag agc aag gtc ttc gag gcc gtc agc ccg agc agc gag gac tgc     336
Met Gln Ser Lys Val Phe Glu Ala Val Ser Pro Ser Ser Glu Asp Cys
               100                 105                 110 ctc acc atc aac gtc gtg cgc ccc cca ggc act aag gcc ggc gcc aat     384
Leu Thr Ile Asn Val Val Arg Pro Pro Gly Thr Lys Ala Gly Ala Asn
           115                 120                 125
```

-continued

| | | |
|---|---|---|
| ctg cct gtg atg ctg tgg ata ttc ggg ggc ggc ttc gaa gtc gga ggc<br>Leu Pro Val Met Leu Trp Ile Phe Gly Gly Gly Phe Glu Val Gly Gly<br>130                    135                    140 | 432 |
| acc tcg acg ttc ccg ccc gcc caa atg ata aca aag tct ata gcg atg<br>Thr Ser Thr Phe Pro Pro Ala Gln Met Ile Thr Lys Ser Ile Ala Met<br>145                    150                    155                    160 | 480 |
| ggg aag cca ata ata cac gtc tca gtc aat tac agg gtc agt agc tgg<br>Gly Lys Pro Ile Ile His Val Ser Val Asn Tyr Arg Val Ser Ser Trp<br>                    165                    170                    175 | 528 |
| ggt ttt ctc gct gga gat gaa atc aaa gca gag ggc tcc gcc aat gcg<br>Gly Phe Leu Ala Gly Asp Glu Ile Lys Ala Glu Gly Ser Ala Asn Ala<br>180                    185                    190 | 576 |
| ggg ttg aaa gat caa agg ctt ggt atg caa tgg gtg gct gat aat att<br>Gly Leu Lys Asp Gln Arg Leu Gly Met Gln Trp Val Ala Asp Asn Ile<br>                    195                    200                    205 | 624 |
| gca gcc ttt gga ggc gat cct act aaa gtc acc ata ttt ggg gaa tcg<br>Ala Ala Phe Gly Gly Asp Pro Thr Lys Val Thr Ile Phe Gly Glu Ser<br>210                    215                    220 | 672 |
| gcg ggt tct atg tca gtt atg tgt cac atc cta tgg aac gac gga gat<br>Ala Gly Ser Met Ser Val Met Cys His Ile Leu Trp Asn Asp Gly Asp<br>225                    230                    235                    240 | 720 |
| aat acg tac aaa ggc aaa ccg tta ttt cgc gct ggg atc atg caa agt<br>Asn Thr Tyr Lys Gly Lys Pro Leu Phe Arg Ala Gly Ile Met Gln Ser<br>                    245                    250                    255 | 768 |
| ggt gca atg gta ccc agc gat gcg gtc gat gga atc tat ggc aat gag<br>Gly Ala Met Val Pro Ser Asp Ala Val Asp Gly Ile Tyr Gly Asn Glu<br>260                    265                    270 | 816 |
| atc ttt gat ctg ctc gcg tcc aat gct ggg tgc ggt tcg gca tct gat<br>Ile Phe Asp Leu Leu Ala Ser Asn Ala Gly Cys Gly Ser Ala Ser Asp<br>                    275                    280                    285 | 864 |
| aag ttg gcc tgc ctt cgg gga gtg tca agt gat aca cta gag gat gcg<br>Lys Leu Ala Cys Leu Arg Gly Val Ser Ser Asp Thr Leu Glu Asp Ala<br>290                    295                    300 | 912 |
| act aat aat acc cca ggc ttc tta gct tat agc tcc ctg cgt ctc tcg<br>Thr Asn Asn Thr Pro Gly Phe Leu Ala Tyr Ser Ser Leu Arg Leu Ser<br>305                    310                    315                    320 | 960 |
| tat ttg cct cga ccg gac ggg gtg aac att acg gat gac atg tat gca<br>Tyr Leu Pro Arg Pro Asp Gly Val Asn Ile Thr Asp Asp Met Tyr Ala<br>                    325                    330                    335 | 1008 |
| ctt gtg aga gag ggt aaa tat gcc aat att ccc gtg att att gga gac<br>Leu Val Arg Glu Gly Lys Tyr Ala Asn Ile Pro Val Ile Ile Gly Asp<br>340                    345                    350 | 1056 |
| cag aac gac gag ggc aca ttc ttc ggg act tct tca cta aac gtc acc<br>Gln Asn Asp Glu Gly Thr Phe Phe Gly Thr Ser Ser Leu Asn Val Thr<br>                    355                    360                    365 | 1104 |
| acg gac gcg caa gct agg gag tac ttt aag cag agt ttt gtt cat gca<br>Thr Asp Ala Gln Ala Arg Glu Tyr Phe Lys Gln Ser Phe Val His Ala<br>370                    375                    380 | 1152 |
| agc gac gcc gag att gac aca tta atg act gcg tac cca ggt gac att<br>Ser Asp Ala Glu Ile Asp Thr Leu Met Thr Ala Tyr Pro Gly Asp Ile<br>385                    390                    395                    400 | 1200 |
| acc caa gga tcc cct ttc gac acg ggc atc ctg aac gct ctc aca ccg<br>Thr Gln Gly Ser Pro Phe Asp Thr Gly Ile Leu Asn Ala Leu Thr Pro<br>                    405                    410                    415 | 1248 |
| cag ttt aag cgc atc tcg gca gta ttg ggg gac ctt ggt ttc act cta<br>Gln Phe Lys Arg Ile Ser Ala Val Leu Gly Asp Leu Gly Phe Thr Leu<br>420                    425                    430 | 1296 |
| gcc cgg cgt tat ttc tta aac cac tac acc gga ggc acg aag tac tct<br>Ala Arg Arg Tyr Phe Leu Asn His Tyr Thr Gly Gly Thr Lys Tyr Ser | 1344 |

```
                435                 440                 445
ttc ctg tca aag cag ctc agt ggc ttg ccc gtg ctt ggt aca ttc cac        1392
Phe Leu Ser Lys Gln Leu Ser Gly Leu Pro Val Leu Gly Thr Phe His
    450                 455                 460 agc aac gac atc gtc ttc cag gac tac ctg ctc gga tcc ggc tct ctt        1440
Ser Asn Asp Ile Val Phe Gln Asp Tyr Leu Leu Gly Ser Gly Ser Leu
465                 470                 475                 480 atc tac aat aat gct ttc att gct ttc gct acg gat ctt gat cca aat        1488
Ile Tyr Asn Asn Ala Phe Ile Ala Phe Ala Thr Asp Leu Asp Pro Asn
                485                 490                 495 acg gct ggt ctt ctt gtt aag tgg cca gag tac aca tct tct tct cag        1536
Thr Ala Gly Leu Leu Val Lys Trp Pro Glu Tyr Thr Ser Ser Ser Gln
        500                 505                 510 tct ggt aat aat ctt atg atg att aat gct ctt ggt ctt tac acg ggt        1584
Ser Gly Asn Asn Leu Met Met Ile Asn Ala Leu Gly Leu Tyr Thr Gly
            515                 520                 525 aag gat aat ttc aga aca gct ggt tac gat gct ctt ttc tct aat cca        1632
Lys Asp Asn Phe Arg Thr Ala Gly Tyr Asp Ala Leu Phe Ser Asn Pro
530                 535                 540 cca tct ttc ttc gtt tag                                                1650
Pro Ser Phe Phe Val *
545
```

<210> SEQ ID NO 2
<211> LENGTH: 549
<212> TYPE: PRT
<213> ORGANISM: Artificial Sequence
<220> FEATURE:
<223> OTHER INFORMATION: Synthetic lipase from C. cylindracea

<400> SEQUENCE: 2

```
Met Glu Leu Ala Leu Ala Leu Ser Leu Ile Ala Ser Val Ala Ala Ala
1               5                   10                  15

Pro Thr Ala Thr Leu Ala Asn Gly Asp Thr Ile Thr Gly Leu Asn Ala
            20                  25                  30

Ile Ile Asn Glu Ala Phe Leu Gly Ile Pro Phe Ala Glu Pro Pro Val
        35                  40                  45

Gly Asn Leu Arg Phe Lys Asp Pro Val Pro Tyr Ser Gly Ser Leu Asp
    50                  55                  60

Gly Gln Lys Phe Thr Ser Tyr Gly Pro Ser Cys Met Gln Gln Asn Pro
65                  70                  75                  80

Glu Gly Thr Tyr Glu Glu Asn Leu Pro Lys Ala Ala Leu Asp Leu Val
                85                  90                  95

Met Gln Ser Lys Val Phe Glu Ala Val Ser Pro Ser Ser Glu Asp Cys
            100                 105                 110

Leu Thr Ile Asn Val Val Arg Pro Pro Gly Thr Lys Ala Gly Ala Asn
        115                 120                 125

Leu Pro Val Met Leu Trp Ile Phe Gly Gly Gly Phe Glu Val Gly Gly
    130                 135                 140

Thr Ser Thr Phe Pro Pro Ala Gln Met Ile Thr Lys Ser Ile Ala Met
145                 150                 155                 160

Gly Lys Pro Ile Ile His Val Ser Val Asn Tyr Arg Val Ser Ser Trp
                165                 170                 175

Gly Phe Leu Ala Gly Asp Glu Ile Lys Ala Glu Gly Ser Ala Asn Ala
            180                 185                 190

Gly Leu Lys Asp Gln Arg Leu Gly Met Gln Trp Val Ala Asp Asn Ile
        195                 200                 205
```

```
Ala Ala Phe Gly Gly Asp Pro Thr Lys Val Thr Ile Phe Gly Glu Ser
    210                 215                 220
Ala Gly Ser Met Ser Val Met Cys His Ile Leu Trp Asn Asp Gly Asp
225                 230                 235                 240
Asn Thr Tyr Lys Gly Lys Pro Leu Phe Arg Ala Gly Ile Met Gln Ser
                245                 250                 255
Gly Ala Met Val Pro Ser Asp Ala Val Asp Gly Ile Tyr Gly Asn Glu
            260                 265                 270
Ile Phe Asp Leu Leu Ala Ser Asn Ala Gly Cys Gly Ser Ala Ser Asp
        275                 280                 285
Lys Leu Ala Cys Leu Arg Gly Val Ser Ser Asp Thr Leu Glu Asp Ala
    290                 295                 300
Thr Asn Asn Thr Pro Gly Phe Leu Ala Tyr Ser Ser Leu Arg Leu Ser
305                 310                 315                 320
Tyr Leu Pro Arg Pro Asp Gly Val Asn Ile Thr Asp Asp Met Tyr Ala
                325                 330                 335
Leu Val Arg Glu Gly Lys Tyr Ala Asn Ile Pro Val Ile Ile Gly Asp
            340                 345                 350
Gln Asn Asp Glu Gly Thr Phe Phe Gly Thr Ser Ser Leu Asn Val Thr
        355                 360                 365
Thr Asp Ala Gln Ala Arg Glu Tyr Phe Lys Gln Ser Phe Val His Ala
    370                 375                 380
Ser Asp Ala Glu Ile Asp Thr Leu Met Thr Ala Tyr Pro Gly Asp Ile
385                 390                 395                 400
Thr Gln Gly Ser Pro Phe Asp Thr Gly Ile Leu Asn Ala Leu Thr Pro
                405                 410                 415
Gln Phe Lys Arg Ile Ser Ala Val Leu Gly Asp Leu Gly Phe Thr Leu
            420                 425                 430
Ala Arg Arg Tyr Phe Leu Asn His Tyr Thr Gly Gly Thr Lys Tyr Ser
        435                 440                 445
Phe Leu Ser Lys Gln Leu Ser Gly Leu Pro Val Leu Gly Thr Phe His
    450                 455                 460
Ser Asn Asp Ile Val Phe Gln Asp Tyr Leu Leu Gly Ser Gly Ser Leu
465                 470                 475                 480
Ile Tyr Asn Asn Ala Phe Ile Ala Phe Ala Thr Asp Leu Asp Pro Asn
                485                 490                 495
Thr Ala Gly Leu Leu Val Lys Trp Pro Glu Tyr Thr Ser Ser Ser Gln
            500                 505                 510
Ser Gly Asn Asn Leu Met Met Ile Asn Ala Leu Gly Leu Tyr Thr Gly
        515                 520                 525
Lys Asp Asn Phe Arg Thr Ala Gly Tyr Asp Ala Leu Phe Ser Asn Pro
    530                 535                 540
Pro Ser Phe Phe Val
545
```

<210> SEQ ID NO 3
<211> LENGTH: 1350
<212> TYPE: DNA
<213> ORGANISM: Artificial Sequence
<220> FEATURE:
<223> OTHER INFORMATION: Maize-optimized coding sequence for porcine
      pancreatic lipase (not including atg start codon)
<220> FEATURE:
<221> NAME/KEY: CDS
<222> LOCATION: (1)...(1350)

<400> SEQUENCE: 3

| | |
|---|---|
| tcc gag gtg tgc ttc ccg cgc ctc ggc tgc ttc tcc gac gac gcc ccg<br>Ser Glu Val Cys Phe Pro Arg Leu Gly Cys Phe Ser Asp Asp Ala Pro<br>1                     5                            10                      15 | 48 |
| tgg gcc ggc atc gtg cag cgc ccg ctc aag atc ctc ccg tgg tcc ccg<br>Trp Ala Gly Ile Val Gln Arg Pro Leu Lys Ile Leu Pro Trp Ser Pro<br>                20                       25                       30 | 96 |
| aag gac gtg gac acc cgc ttc ctc ctc tac acc aac cag aac cag aac<br>Lys Asp Val Asp Thr Arg Phe Leu Leu Tyr Thr Asn Gln Asn Gln Asn<br>                   35                      40                      45 | 144 |
| aac tac cag gag ctc gtg gcc gac ccg tcc acc atc acc aac tcc aac<br>Asn Tyr Gln Glu Leu Val Ala Asp Pro Ser Thr Ile Thr Asn Ser Asn<br>    50                         55                        60 | 192 |
| ttc cgc atg gac cgc aag acc cgc ttc atc atc cac ggc ttc atc gac<br>Phe Arg Met Asp Arg Lys Thr Arg Phe Ile Ile His Gly Phe Ile Asp<br>65                     70                      75                      80 | 240 |
| aag ggc gag gag gac tgg ctc tcc aac atc tgc aag aac ctc ttc aag<br>Lys Gly Glu Glu Asp Trp Leu Ser Asn Ile Cys Lys Asn Leu Phe Lys<br>                   85                      90                      95 | 288 |
| gtg gag tcc gtg aac tgc atc tgc gtg gac tgg aag ggc ggc tcc cgc<br>Val Glu Ser Val Asn Cys Ile Cys Val Asp Trp Lys Gly Gly Ser Arg<br>                100                     105                     110 | 336 |
| acc ggc tac acc cag gcc tcc cag aac atc cgc atc gtg ggc gcc gag<br>Thr Gly Tyr Thr Gln Ala Ser Gln Asn Ile Arg Ile Val Gly Ala Glu<br>          115                     120                     125 | 384 |
| gtg gcc tac ttc gtg gag gtg ctc aag tcc tcc ctc ggc tac tcc ccg<br>Val Ala Tyr Phe Val Glu Val Leu Lys Ser Ser Leu Gly Tyr Ser Pro<br>130                     135                     140 | 432 |
| tcc aac gtg cac gtg atc ggc cac tcc ctc ggc tcc cac gcc gcc ggc<br>Ser Asn Val His Val Ile Gly His Ser Leu Gly Ser His Ala Ala Gly<br>145                     150                     155                    160 | 480 |
| gag gcc ggc cgc cgc acc aac ggc acc atc gag cgc atc acc ggc ctc<br>Glu Ala Gly Arg Arg Thr Asn Gly Thr Ile Glu Arg Ile Thr Gly Leu<br>                  165                     170                     175 | 528 |
| gac ccg gcc gag ccg tgc ttc cag ggc acc ccg gag ctc gtg cgc ctc<br>Asp Pro Ala Glu Pro Cys Phe Gln Gly Thr Pro Glu Leu Val Arg Leu<br>          180                     185                     190 | 576 |
| gac ccg tcc gac gcc aag ttc gtg gac gtg atc cac acc gac gcc gcc<br>Asp Pro Ser Asp Ala Lys Phe Val Asp Val Ile His Thr Asp Ala Ala<br>                195                     200                     205 | 624 |
| ccg atc atc ccg aac ctc ggc ttc ggc atg tcc cag acc gtg ggc cac<br>Pro Ile Ile Pro Asn Leu Gly Phe Gly Met Ser Gln Thr Val Gly His<br>210                     215                     220 | 672 |
| ctc gac ttc ttc ccg aac ggc ggc aag cag atg ccg ggc tgc cag aag<br>Leu Asp Phe Phe Pro Asn Gly Gly Lys Gln Met Pro Gly Cys Gln Lys<br>225                     230                     235                    240 | 720 |
| aac atc ctc tcc cag atc gtg gac atc gac ggc atc tgg gag ggc acc<br>Asn Ile Leu Ser Gln Ile Val Asp Ile Asp Gly Ile Trp Glu Gly Thr<br>                  245                     250                     255 | 768 |
| cgc gac ttc gtg gcc tgc aac cac ctc cgc tcc tac aag tac tac gcc<br>Arg Asp Phe Val Ala Cys Asn His Leu Arg Ser Tyr Lys Tyr Tyr Ala<br>          260                     265                     270 | 816 |
| gac tcc atc ctc aac ccg gac ggc ttc gcc ggc ttc ccg tgc gac tcc<br>Asp Ser Ile Leu Asn Pro Asp Gly Phe Ala Gly Phe Pro Cys Asp Ser<br>275                     280                     285 | 864 |
| tac aac gtg ttc acc gcc aac aag tgc ttc ccg tgc ccg tcc gag ggc<br>Tyr Asn Val Phe Thr Ala Asn Lys Cys Phe Pro Cys Pro Ser Glu Gly<br>                290                     295                     300 | 912 |
| tgc ccg cag atg ggc cac tac gcc gac cgc ttc ccg ggc aag acc aac<br>Cys Pro Gln Met Gly His Tyr Ala Asp Arg Phe Pro Gly Lys Thr Asn | 960 |

```
                305                 310                 315                 320
ggc gtg tcc cag gtg ttc tac ctc aac acc ggc gac gcc tcc aac ttc          1008
Gly Val Ser Gln Val Phe Tyr Leu Asn Thr Gly Asp Ala Ser Asn Phe
                    325                 330                 335 gcc cgc tgg cgc tac aag gtg tcc gtg acc ctc tcc ggc aag aag gtg          1056
Ala Arg Trp Arg Tyr Lys Val Ser Val Thr Leu Ser Gly Lys Lys Val
            340                 345                 350 acc ggc cac atc ctc gtg tcc ctc ttc ggc aac gag ggc aac tcc cgc          1104
Thr Gly His Ile Leu Val Ser Leu Phe Gly Asn Glu Gly Asn Ser Arg
        355                 360                 365 cag tac gag atc tac aag ggc acc ctc cag ccg gac aac acc cac tcc          1152
Gln Tyr Glu Ile Tyr Lys Gly Thr Leu Gln Pro Asp Asn Thr His Ser
    370                 375                 380 gac gag ttc gac tcc gac gtg gag gtg ggc gac ctc cag aag gtg aag          1200
Asp Glu Phe Asp Ser Asp Val Glu Val Gly Asp Leu Gln Lys Val Lys
385                 390                 395                 400 ttc atc tgg tac aac aac aac gtg atc aac ccg acc ctc ccg cgc gtg          1248
Phe Ile Trp Tyr Asn Asn Asn Val Ile Asn Pro Thr Leu Pro Arg Val
                405                 410                 415 ggc gcc tcc aag atc acc gtg gag cgc aac gac ggc aag gtg tac gac          1296
Gly Ala Ser Lys Ile Thr Val Glu Arg Asn Asp Gly Lys Val Tyr Asp
            420                 425                 430 ttc tgc tcc cag gag acc gtg cgc gag gag gtg ctc ctc acc ctc aac          1344
Phe Cys Ser Gln Glu Thr Val Arg Glu Glu Val Leu Leu Thr Leu Asn
        435                 440                 445 ccg tgc                                                                    1350
Pro Cys
    450

<210> SEQ ID NO 4
<211> LENGTH: 450
<212> TYPE: PRT
<213> ORGANISM: Sus scrofa

<400> SEQUENCE: 4

Ser Glu Val Cys Phe Pro Arg Leu Gly Cys Phe Ser Asp Asp Ala Pro
1               5                   10                  15

Trp Ala Gly Ile Val Gln Arg Pro Leu Lys Ile Leu Pro Trp Ser Pro
            20                  25                  30

Lys Asp Val Asp Thr Arg Phe Leu Leu Tyr Thr Asn Gln Asn Gln Asn
        35                  40                  45

Asn Tyr Gln Glu Leu Val Ala Asp Pro Ser Thr Ile Thr Asn Ser Asn
    50                  55                  60

Phe Arg Met Asp Arg Lys Thr Arg Phe Ile Ile His Gly Phe Ile Asp
65                  70                  75                  80

Lys Gly Glu Glu Asp Trp Leu Ser Asn Ile Cys Lys Asn Leu Phe Lys
                85                  90                  95

Val Glu Ser Val Asn Cys Ile Cys Val Asp Trp Lys Gly Gly Ser Arg
            100                 105                 110

Thr Gly Tyr Thr Gln Ala Ser Gln Asn Ile Arg Ile Val Gly Ala Glu
        115                 120                 125

Val Ala Tyr Phe Val Glu Val Leu Lys Ser Ser Leu Gly Tyr Ser Pro
    130                 135                 140

Ser Asn Val His Val Ile Gly His Ser Leu Gly Ser His Ala Ala Gly
145                 150                 155                 160

Glu Ala Gly Arg Arg Thr Asn Gly Thr Ile Glu Arg Ile Thr Gly Leu
                165                 170                 175
```

-continued

```
Asp Pro Ala Glu Pro Cys Phe Gln Gly Thr Pro Glu Leu Val Arg Leu
            180                 185                 190
Asp Pro Ser Asp Ala Lys Phe Val Asp Val Ile His Thr Asp Ala Ala
        195                 200                 205
Pro Ile Ile Pro Asn Leu Gly Phe Gly Met Ser Gln Thr Val Gly His
    210                 215                 220
Leu Asp Phe Phe Pro Asn Gly Gly Lys Gln Met Pro Gly Cys Gln Lys
225                 230                 235                 240
Asn Ile Leu Ser Gln Ile Val Asp Ile Asp Gly Ile Trp Glu Gly Thr
                245                 250                 255
Arg Asp Phe Val Ala Cys Asn His Leu Arg Ser Tyr Lys Tyr Tyr Ala
            260                 265                 270
Asp Ser Ile Leu Asn Pro Asp Gly Phe Ala Gly Phe Pro Cys Asp Ser
        275                 280                 285
Tyr Asn Val Phe Thr Ala Asn Lys Cys Phe Pro Cys Pro Ser Glu Gly
    290                 295                 300
Cys Pro Gln Met Gly His Tyr Ala Asp Arg Phe Pro Gly Lys Thr Asn
305                 310                 315                 320
Gly Val Ser Gln Val Phe Tyr Leu Asn Thr Gly Asp Ala Ser Asn Phe
                325                 330                 335
Ala Arg Trp Arg Tyr Lys Val Ser Val Thr Leu Ser Gly Lys Lys Val
            340                 345                 350
Thr Gly His Ile Leu Val Ser Leu Phe Gly Asn Glu Gly Asn Ser Arg
        355                 360                 365
Gln Tyr Glu Ile Tyr Lys Gly Thr Leu Gln Pro Asp Asn Thr His Ser
    370                 375                 380
Asp Glu Phe Asp Ser Asp Val Glu Val Gly Asp Leu Gln Lys Val Lys
385                 390                 395                 400
Phe Ile Trp Tyr Asn Asn Asn Val Ile Asn Pro Thr Leu Pro Arg Val
                405                 410                 415
Gly Ala Ser Lys Ile Thr Val Glu Arg Asn Asp Gly Lys Val Tyr Asp
            420                 425                 430
Phe Cys Ser Gln Glu Thr Val Arg Glu Glu Val Leu Leu Thr Leu Asn
        435                 440                 445
Pro Cys
    450
```

<210> SEQ ID NO 5
<211> LENGTH: 3120
<212> TYPE: DNA
<213> ORGANISM: Rhizopus arrhizus
<220> FEATURE:
<221> NAME/KEY: CDS
<222> LOCATION: (901)...(2079)

<400> SEQUENCE: 5

```
tatagtatag atactggtga gatagaacaa atggagcgcg tatacaaaat aaatttaggg      60
tcatcttaaa tttgagttca ttatagggcc tttttctgct gggaaaagga cacaaagttc     120
gataacattc ttggtcaata caagataatt gaatgcttgt gtttaatgag cttttatgct     180
atttcatgat ctattctaga tcatgagata aacttatgtg ctcaataaat aaaattcttt     240
tcttaacaaa gtctttaatt tgatgaagtg atcaagtaat ccttgtgcct tataattgaa     300
ggatgatcaa gtttgtgctt caataaaata agttgcataa tgcattggct ttttatattt     360
taataacatt tctattaact cgaaatatct ttcaaaataa gcttcatatc aattttttgcc     420
```

-continued

```
ttgtttcttc caactgccta caacactaaa ttgaaataag tccggtttta cttttttcaat    480 gggagaaaat ggctgaattc ttttgaaagt taagttatac attttcagct ttactgtcgc    540
acataaaatt agtttatttt atcccagcga gtgatatagg aaaaatcaga attgtctcct    600 tttttttgtct tattttatgt aaaatccgct tgtgtgatg ttttgtatta cattcaaaaa    660
aagaggaatc gctcgtaaca ataattgatc acttggtact actattaaat atacctaatt    720
tcatgagggg ttacaatgtg cgtggataaa ttgccattgg tctctctatt ttttgaacaa    780
aaaaaaacat ataaatagag caagtttatt ttatgttcaa gctctctatc ttactaagct    840
aattgataca gactcttctt ttcttttctt cttacccctt ccagttcttt actatcaaac    900
```

| | | | | | | | | | | | | | | | | |
|---|---|---|---|---|---|---|---|---|---|---|---|---|---|---|---|---|
| atg | gtt | tca | ttc | att | tcc | att | tct | caa | ggt | gtt | agt | ctt | tgt | ctt | ctt | 948 |
| Met | Val | Ser | Phe | Ile | Ser | Ile | Ser | Gln | Gly | Val | Ser | Leu | Cys | Leu | Leu | |
| 1 | | | | 5 | | | | | 10 | | | | | 15 | | |

| gtc | tct | tcc | atg | atg | ctc | ggt | tca | tct | gct | gtt | cct | gtt | tct | ggt | aaa | 996 |
|---|---|---|---|---|---|---|---|---|---|---|---|---|---|---|---|---|
| Val | Ser | Ser | Met | Met | Leu | Gly | Ser | Ser | Ala | Val | Pro | Val | Ser | Gly | Lys | |
| | | | 20 | | | | | 25 | | | | | 30 | | | |

| tct | gga | tct | tcc | act | acc | gcc | gtc | tct | gca | tct | gac | aat | tct | gcc | ctc | 1044 |
|---|---|---|---|---|---|---|---|---|---|---|---|---|---|---|---|---|
| Ser | Gly | Ser | Ser | Thr | Thr | Ala | Val | Ser | Ala | Ser | Asp | Asn | Ser | Ala | Leu | |
| | | 35 | | | | | 40 | | | | | 45 | | | | |

| cct | cct | ctc | att | tcc | agc | cgt | tgt | gct | cct | cct | tct | aac | aag | gga | agt | 1092 |
|---|---|---|---|---|---|---|---|---|---|---|---|---|---|---|---|---|
| Pro | Pro | Leu | Ile | Ser | Ser | Arg | Cys | Ala | Pro | Pro | Ser | Asn | Lys | Gly | Ser | |
| | 50 | | | | | 55 | | | | | 60 | | | | | |

| aaa | agc | gat | ctt | caa | gct | gaa | cct | tac | tac | atg | caa | aag | aat | aca | gaa | 1140 |
|---|---|---|---|---|---|---|---|---|---|---|---|---|---|---|---|---|
| Lys | Ser | Asp | Leu | Gln | Ala | Glu | Pro | Tyr | Tyr | Met | Gln | Lys | Asn | Thr | Glu | |
| 65 | | | | | 70 | | | | | 75 | | | | | 80 | |

| tgg | tat | gag | tcc | cat | ggt | ggc | aac | ctg | aca | tcc | atc | gga | aag | cga | gat | 1188 |
|---|---|---|---|---|---|---|---|---|---|---|---|---|---|---|---|---|
| Trp | Tyr | Glu | Ser | His | Gly | Gly | Asn | Leu | Thr | Ser | Ile | Gly | Lys | Arg | Asp | |
| | | | | 85 | | | | | 90 | | | | | 95 | | |

| gac | aat | ttg | gtt | ggt | ggc | atg | act | ttg | gat | tta | cct | agc | gat | gct | cct | 1236 |
|---|---|---|---|---|---|---|---|---|---|---|---|---|---|---|---|---|
| Asp | Asn | Leu | Val | Gly | Gly | Met | Thr | Leu | Asp | Leu | Pro | Ser | Asp | Ala | Pro | |
| | | | 100 | | | | | 105 | | | | | 110 | | | |

| cct | atc | agc | ctc | tct | gga | tct | acc | aac | agc | gcc | tct | gat | ggt | ggt | aag | 1284 |
|---|---|---|---|---|---|---|---|---|---|---|---|---|---|---|---|---|
| Pro | Ile | Ser | Leu | Ser | Gly | Ser | Thr | Asn | Ser | Ala | Ser | Asp | Gly | Gly | Lys | |
| | | 115 | | | | | 120 | | | | | 125 | | | | |

| gtt | gtt | gct | gct | act | act | gct | caa | att | caa | gag | ttc | acc | aag | tat | gct | 1332 |
|---|---|---|---|---|---|---|---|---|---|---|---|---|---|---|---|---|
| Val | Val | Ala | Ala | Thr | Thr | Ala | Gln | Ile | Gln | Glu | Phe | Thr | Lys | Tyr | Ala | |
| | 130 | | | | | 135 | | | | | 140 | | | | | |

| ggt | atc | gct | gcc | act | gcc | tac | tgt | cgt | tct | gtt | gtc | cct | ggt | aac | aag | 1380 |
|---|---|---|---|---|---|---|---|---|---|---|---|---|---|---|---|---|
| Gly | Ile | Ala | Ala | Thr | Ala | Tyr | Cys | Arg | Ser | Val | Val | Pro | Gly | Asn | Lys | |
| 145 | | | | | 150 | | | | | 155 | | | | | 160 | |

| tgg | gac | tgt | gtc | caa | tgt | caa | aag | tgg | gtt | cct | gat | ggc | aag | atc | atc | 1428 |
|---|---|---|---|---|---|---|---|---|---|---|---|---|---|---|---|---|
| Trp | Asp | Cys | Val | Gln | Cys | Gln | Lys | Trp | Val | Pro | Asp | Gly | Lys | Ile | Ile | |
| | | | | 165 | | | | | 170 | | | | | 175 | | |

| act | acc | ttt | acc | tcc | ttg | ctt | tcc | gac | aca | aat | ggt | tac | gtc | ttg | aga | 1476 |
|---|---|---|---|---|---|---|---|---|---|---|---|---|---|---|---|---|
| Thr | Thr | Phe | Thr | Ser | Leu | Leu | Ser | Asp | Thr | Asn | Gly | Tyr | Val | Leu | Arg | |
| | | | 180 | | | | | 185 | | | | | 190 | | | |

| agt | gat | aaa | caa | aag | acc | att | tat | ctt | gtt | ttc | cgt | ggt | acc | aac | tcc | 1524 |
|---|---|---|---|---|---|---|---|---|---|---|---|---|---|---|---|---|
| Ser | Asp | Lys | Gln | Lys | Thr | Ile | Tyr | Leu | Val | Phe | Arg | Gly | Thr | Asn | Ser | |
| | | 195 | | | | | 200 | | | | | 205 | | | | |

| ttc | aga | agt | gcc | atc | act | gat | att | gtc | ttc | aac | ttt | tcc | gac | tac | aag | 1572 |
|---|---|---|---|---|---|---|---|---|---|---|---|---|---|---|---|---|
| Phe | Arg | Ser | Ala | Ile | Thr | Asp | Ile | Val | Phe | Asn | Phe | Ser | Asp | Tyr | Lys | |
| | 210 | | | | | 215 | | | | | 220 | | | | | |

| cct | gtc | aag | ggc | gcc | aag | gtt | cat | gct | ggt | ttc | ctt | tcc | tct | tat | gag | 1620 |
|---|---|---|---|---|---|---|---|---|---|---|---|---|---|---|---|---|
| Pro | Val | Lys | Gly | Ala | Lys | Val | His | Ala | Gly | Phe | Leu | Ser | Ser | Tyr | Glu | |
| 225 | | | | | 230 | | | | | 235 | | | | | 240 | |

| caa | gtt | gtc | aat | gac | tat | ttc | cct | gtc | gtc | caa | gaa | caa | ctg | acc | gcc | 1668 |
|---|---|---|---|---|---|---|---|---|---|---|---|---|---|---|---|---|
| Gln | Val | Val | Asn | Asp | Tyr | Phe | Pro | Val | Val | Gln | Glu | Gln | Leu | Thr | Ala | |
| | | | | 245 | | | | | 250 | | | | | 255 | | |

```
aac cct act tac aag gtc atc gtc acc ggt cac tca ctc ggt ggt gca       1716
Asn Pro Thr Tyr Lys Val Ile Val Thr Gly His Ser Leu Gly Gly Ala
            260                 265                 270 caa gct ttg ctt gcc ggt atg gat ctc tac caa cgt gaa cca aga ctg       1764
Gln Ala Leu Leu Ala Gly Met Asp Leu Tyr Gln Arg Glu Pro Arg Leu
        275                 280                 285 tct ccc aag aat ttg agc atc ttc act gtt ggt ggt cct cgt gtt ggt       1812
Ser Pro Lys Asn Leu Ser Ile Phe Thr Val Gly Gly Pro Arg Val Gly
        290                 295                 300 aac ccc acc ttt gct tac tat gtt gaa tct acc ggt att cct ttc caa       1860
Asn Pro Thr Phe Ala Tyr Tyr Val Glu Ser Thr Gly Ile Pro Phe Gln
305                 310                 315                 320 cgt acc gtt cac aag aga gat atc gtt cct cac gtt cct cct caa tcc       1908
Arg Thr Val His Lys Arg Asp Ile Val Pro His Val Pro Pro Gln Ser
                325                 330                 335 ttc gga ttc ctt cat ccc ggt gtt gaa tct tgg att aag tct ggt acc       1956
Phe Gly Phe Leu His Pro Gly Val Glu Ser Trp Ile Lys Ser Gly Thr
            340                 345                 350 tcc aac gtt caa atc tgt act tct gaa att gaa acc aag gat tgc agt       2004
Ser Asn Val Gln Ile Cys Thr Ser Glu Ile Glu Thr Lys Asp Cys Ser
        355                 360                 365 aac tct atc gtt cct ttc acc tct ctc ctt gat cac ttg agt tac ttt       2052
Asn Ser Ile Val Pro Phe Thr Ser Leu Leu Asp His Leu Ser Tyr Phe
        370                 375                 380 gat atc aac gaa gga agc tgt ttg taa aacacttgac gtgttactct              2099
Asp Ile Asn Glu Gly Ser Cys Leu  *
385                 390 aattttataa taaaactaag ttttatacaa ataactttt gcatgtctac atataattta      2159
gaatgtaacc tcaacttcaa acttgtatat cagtagtctc ttatcatttc atctggtcca     2219
tttttaaaac tatgttcata gagtcattta cattagacat attctatgat atcctctgat    2279
ctacagtctt catttattct tttatgattc acgtaatgtc ttgagtttag aaaaaatagt    2339
ttaagagttt ttttgtagtt aaaaaattaa tctctgcctt tttttaggat ttaaatatta    2399
taatgtttta cataacttga aacccatacc aaagtatttt agtgttattt tactaataaa    2459
ataaaaccta ttgcttgtga agccaattga ttttgtgct tatttcataa atttggtttt    2519
attttaggga agaaataaca caaggtgcaa agtagattgt ttataaggaa aaggattgaa    2579
attgactaga acaaccatca atattatttg cagagtagac atattaggct aatctgagtt    2639
atctatcctc tcgttatatt tagcctaaaa tgctgttatt ataagcattt tgcagtatct    2699
gtaatttgct gaaatacttg caagaaacat atttgttatt gaactaagat taactaaata    2759 cttttctttta ttttccttt ttttgacaat cataattgtt gtctatttgt gcttaattca   2819
gcttttaaag aagggcgatt aaccagatta atttaatt tcataatctt cttcttctcc    2879
tgctgttact ttcaaaatct tgggcgcttc atttgctgtt attttatgag tttatgtata    2939
ttaaagctac gaagtattgc tttctgtttg ttttacatta ctaacttgct actcttgtat   2999
cttattcaga agacctttca tcttttcttt agtgttgtct agctacgtat attttttttg   3059
ttaggtcttc ttatctgttt cttataatta tagtatcttt ttttctgaga ataaatgttt   3119
t                                                                     3120
```

<210> SEQ ID NO 6
<211> LENGTH: 392
<212> TYPE: PRT
<213> ORGANISM: Rhizopus arrhizus

<400> SEQUENCE: 6

```
Met Val Ser Phe Ile Ser Ile Ser Gln Gly Val Ser Leu Cys Leu Leu
  1               5                  10                  15

Val Ser Ser Met Met Leu Gly Ser Ser Ala Val Pro Val Ser Gly Lys
             20                  25                  30

Ser Gly Ser Ser Thr Thr Ala Val Ser Ala Ser Asp Asn Ser Ala Leu
         35                  40                  45

Pro Pro Leu Ile Ser Ser Arg Cys Ala Pro Pro Ser Asn Lys Gly Ser
     50                  55                  60

Lys Ser Asp Leu Gln Ala Glu Pro Tyr Tyr Met Gln Lys Asn Thr Glu
 65                  70                  75                  80

Trp Tyr Glu Ser His Gly Gly Asn Leu Thr Ser Ile Gly Lys Arg Asp
                 85                  90                  95

Asp Asn Leu Val Gly Gly Met Thr Leu Asp Leu Pro Ser Asp Ala Pro
            100                 105                 110

Pro Ile Ser Leu Ser Gly Ser Thr Asn Ser Ala Ser Asp Gly Gly Lys
            115                 120                 125

Val Val Ala Ala Thr Thr Ala Gln Ile Gln Glu Phe Thr Lys Tyr Ala
130                 135                 140

Gly Ile Ala Ala Thr Ala Tyr Cys Arg Ser Val Val Pro Gly Asn Lys
145                 150                 155                 160

Trp Asp Cys Val Gln Cys Gln Lys Trp Val Pro Asp Gly Lys Ile Ile
                165                 170                 175

Thr Thr Phe Thr Ser Leu Leu Ser Asp Thr Asn Gly Tyr Val Leu Arg
            180                 185                 190

Ser Asp Lys Gln Lys Thr Ile Tyr Leu Val Phe Arg Gly Thr Asn Ser
            195                 200                 205

Phe Arg Ser Ala Ile Thr Asp Ile Val Phe Asn Phe Ser Asp Tyr Lys
    210                 215                 220

Pro Val Lys Gly Ala Lys Val His Ala Gly Phe Leu Ser Ser Tyr Glu
225                 230                 235                 240

Gln Val Val Asn Asp Tyr Phe Pro Val Val Gln Glu Gln Leu Thr Ala
                245                 250                 255

Asn Pro Thr Tyr Lys Val Ile Val Thr Gly His Ser Leu Gly Gly Ala
            260                 265                 270

Gln Ala Leu Leu Ala Gly Met Asp Leu Tyr Gln Arg Glu Pro Arg Leu
            275                 280                 285

Ser Pro Lys Asn Leu Ser Ile Phe Thr Val Gly Gly Pro Arg Val Gly
    290                 295                 300

Asn Pro Thr Phe Ala Tyr Tyr Val Glu Ser Thr Gly Ile Pro Phe Gln
305                 310                 315                 320

Arg Thr Val His Lys Arg Asp Ile Val Pro His Val Pro Pro Gln Ser
                325                 330                 335

Phe Gly Phe Leu His Pro Gly Val Glu Ser Trp Ile Lys Ser Gly Thr
            340                 345                 350

Ser Asn Val Gln Ile Cys Thr Ser Glu Ile Glu Thr Lys Asp Cys Ser
            355                 360                 365

Asn Ser Ile Val Pro Phe Thr Ser Leu Leu Asp His Leu Ser Tyr Phe
    370                 375                 380

Asp Ile Asn Glu Gly Ser Cys Leu
385                 390
```

<210> SEQ ID NO 7

```
<211> LENGTH: 942
<212> TYPE: DNA
<213> ORGANISM: Nitrosomonas europaea
<220> FEATURE:
<221> NAME/KEY: CDS
<222> LOCATION: (1)...(943)

<400> SEQUENCE: 7 atg gag tcg aaa aat gag cct ggg gcg tcc gcc tta ctg cgt gtc ctt      48
Met Glu Ser Lys Asn Glu Pro Gly Ala Ser Ala Leu Leu Arg Val Leu
 1               5                  10                  15 acg ctg gac ggc ggc ggc gcg aag ggc ttt tac acg ctg ggt gta ctc      96
Thr Leu Asp Gly Gly Gly Ala Lys Gly Phe Tyr Thr Leu Gly Val Leu
             20                  25                  30 aag gaa atc gag gcg atg gtc ggg tgc cct ttg cac cag aag ttt gat     144
Lys Glu Ile Glu Ala Met Val Gly Cys Pro Leu His Gln Lys Phe Asp
         35                  40                  45 ctg gtt ttc ggt acc agt acg ggc gcg atc atc gcg tca ctg atc gcg     192
Leu Val Phe Gly Thr Ser Thr Gly Ala Ile Ile Ala Ser Leu Ile Ala
     50                  55                  60 ctc ggc cac agc gtc gat tcc atc ctg gag ctg tac cgc aag cac gtg     240
Leu Gly His Ser Val Asp Ser Ile Leu Glu Leu Tyr Arg Lys His Val
 65                  70                  75                  80 cct acc gtg atg tcg cag aaa acc gct ccg gcc agg tcg cag gcc ttg     288
Pro Thr Val Met Ser Gln Lys Thr Ala Pro Ala Arg Ser Gln Ala Leu
                 85                  90                  95 aag aag cta gct agc gag gtc ttc ggc gat gca acg ttc agt gat gtg     336
Lys Lys Leu Ala Ser Glu Val Phe Gly Asp Ala Thr Phe Ser Asp Val
            100                 105                 110 aag acc ggc atc ggg atc gtc acg gcc aag tgg ctg acc gag cgc cca     384
Lys Thr Gly Ile Gly Ile Val Thr Ala Lys Trp Leu Thr Glu Arg Pro
        115                 120                 125 atc ttc aag ggc agc gtc gcg cag gcg cac ggc caa gtc ggc acg         432
Met Ile Phe Lys Gly Ser Val Ala Gln Ala His Gly Gln Val Gly Thr
130                 135                 140 ttc gtc ccg ggc ttt ggc gtg agc atc gca gac gcc gtc aag gca tcg     480
Phe Val Pro Gly Phe Gly Val Ser Ile Ala Asp Ala Val Lys Ala Ser
145                 150                 155                 160 tgc tcg gcc tac ccg ttc ttc gag cga acg gta gtg agg act tca atg     528
Cys Ser Ala Tyr Pro Phe Phe Glu Arg Thr Val Val Arg Thr Ser Met
                165                 170                 175 ggc gag gac atc gag cta att gac ggc ggg tac tgt gca aac aac ccg     576
Gly Glu Asp Ile Glu Leu Ile Asp Gly Gly Tyr Cys Ala Asn Asn Pro
            180                 185                 190 act ttg tac gcg atc gcc gat gcg gtt cag gcg ctt cgg agt gat cgc     624
Thr Leu Tyr Ala Ile Ala Asp Ala Val Gln Ala Leu Arg Ser Asp Arg
        195                 200                 205 aag gac atc cgg ctg gtg agc gtc ggc gtg ggc atc tac ccc gac ccg     672
Lys Asp Ile Arg Leu Val Ser Val Gly Val Gly Ile Tyr Pro Asp Pro
    210                 215                 220 aag ccg agc ctg ctg atg tgg ttg gcg aag aaa tat ctc gtc agc gtc     720
Lys Pro Ser Leu Leu Met Trp Leu Ala Lys Lys Tyr Leu Val Ser Val
225                 230                 235                 240 cag ttg ctg cag aag acc ctg gag atc aac acg cag tcg atg gac cag     768
Gln Leu Leu Gln Lys Thr Leu Glu Ile Asn Thr Gln Ser Met Asp Gln
                245                 250                 255 ctg cgg cag att ctg ttc cct gac ttg ctg acc atc cgt atc aac gac     816
Leu Arg Gln Ile Leu Phe Pro Asp Leu Leu Thr Ile Arg Ile Asn Asp
            260                 265                 270 tcc tac gtc acg cct gaa atg gcg acc gat ctg ctg gag cac gac ctc     864
Ser Tyr Val Thr Pro Glu Met Ala Thr Asp Leu Leu Glu His Asp Leu
```

-continued

```
            275                 280                 285
aag aag ctg ggc atc ttg ttc cag cga gga cgg gag tcc ttc gcg tcg      912
Lys Lys Leu Gly Ile Leu Phe Gln Arg Gly Arg Glu Ser Phe Ala Ser
    290                 295                 300 cgt gag aag caa ctt cgc gag tat ttg ata                              942
Arg Glu Lys Gln Leu Arg Glu Tyr Leu Ile
305                 310
```

<210> SEQ ID NO 8
<211> LENGTH: 314
<212> TYPE: PRT
<213> ORGANISM: Nitrosomonas europaea

<400> SEQUENCE: 8

```
Met Glu Ser Lys Asn Glu Pro Gly Ala Ser Ala Leu Leu Arg Val Leu
 1               5                  10                  15

Thr Leu Asp Gly Gly Ala Lys Gly Phe Tyr Thr Leu Gly Val Leu
            20                  25                  30

Lys Glu Ile Glu Ala Met Val Gly Cys Pro Leu His Gln Lys Phe Asp
        35                  40                  45

Leu Val Phe Gly Thr Ser Thr Gly Ala Ile Ile Ala Ser Leu Ile Ala
    50                  55                  60

Leu Gly His Ser Val Asp Ser Ile Leu Glu Leu Tyr Arg Lys His Val
65                  70                  75                  80

Pro Thr Val Met Ser Gln Lys Thr Ala Pro Ala Arg Ser Gln Ala Leu
                85                  90                  95

Lys Lys Leu Ala Ser Glu Val Phe Gly Asp Ala Thr Phe Ser Asp Val
            100                 105                 110

Lys Thr Gly Ile Gly Ile Val Thr Ala Lys Trp Leu Thr Glu Arg Pro
        115                 120                 125

Met Ile Phe Lys Gly Ser Val Ala Gln Ala His Gly Gln Val Gly Thr
    130                 135                 140

Phe Val Pro Gly Phe Gly Val Ser Ile Ala Asp Ala Val Lys Ala Ser
145                 150                 155                 160

Cys Ser Ala Tyr Pro Phe Phe Glu Arg Thr Val Val Arg Thr Ser Met
                165                 170                 175

Gly Glu Asp Ile Glu Leu Ile Asp Gly Gly Tyr Cys Ala Asn Asn Pro
            180                 185                 190

Thr Leu Tyr Ala Ile Ala Asp Ala Val Gln Ala Leu Arg Ser Asp Arg
        195                 200                 205

Lys Asp Ile Arg Leu Val Ser Val Gly Val Gly Ile Tyr Pro Asp Pro
    210                 215                 220

Lys Pro Ser Leu Leu Met Trp Leu Ala Lys Lys Tyr Leu Val Ser Val
225                 230                 235                 240

Gln Leu Leu Gln Lys Thr Leu Glu Ile Asn Thr Gln Ser Met Asp Gln
                245                 250                 255

Leu Arg Gln Ile Leu Phe Pro Asp Leu Leu Thr Ile Arg Ile Asn Asp
            260                 265                 270

Ser Tyr Val Thr Pro Glu Met Ala Thr Asp Leu Leu Glu His Asp Leu
        275                 280                 285

Lys Lys Leu Gly Ile Leu Phe Gln Arg Gly Arg Glu Ser Phe Ala Ser
    290                 295                 300

Arg Glu Lys Gln Leu Arg Glu Tyr Leu Ile
305                 310
```

METHODS OF USING NON-PLANT ENCODING NUCLEIC ACIDS

CROSS-REFERENCE TO RELATED APPLICATIONS

This application claims the benefit of U.S. Provisional Application Ser. No. 60/546,605, filed Feb. 20, 2004, the contents of which are herein incorporated by reference in their entirety.

FIELD OF THE INVENTION

The invention relates to compositions and methods for controlling insect species. Additionally, the invention relates to plants and other organisms that have been genetically transformed with the compositions of the invention.

BACKGROUND OF THE INVENTION

Insect pests are a serious problem in agriculture. They destroy millions of acres of staple crops such as corn, soybeans, peas, and cotton. Yearly, these pests cause over $100 billion dollars in crop damage in the U.S. alone. In an ongoing seasonal battle, farmers must apply billions of gallons of synthetic pesticides to combat these pests. However, synthetic pesticides pose many problems. They are expensive, costing U.S. farmers almost $8 billion dollars per year. They force the emergence of insecticide-resistant pests, and they can harm the environment.

Other approaches to pest control have been tried. In some cases, crop growers have introduced "natural predators" of the species sought to be controlled such as non-native insects, fungi, and bacteria like *Bacillus thuringiensis*. Alternatively, crop growers have introduced large colonies of sterile insect pests in the hope that mating between the sterilized insects and fecund wild insects would decrease the insect population. Unfortunately, success has been equivocal and the expense considerable. For example, as a practical matter, introduced species rarely remain on the treated land—spreading to other areas as an unintended consequence. Predator insects migrate, and fungi or bacteria wash off of plants into streams and rivers. Consequently, crop growers need more practical and effective solutions.

One relatively recent solution has been to genetically engineer crops to express plant lipases that have insecticidal properties. Until now, such insecticidal lipases have only been described in certain plants, such as patatin from the potato (U.S. Pat. No. 5,743,477) and pentin from the oil bean tree (U.S. Pat. No. 6,057,491 and U.S. Pat. No. 6,339,144). However, plant-derived lipases have the inherent disadvantage of having induced natural selection pressure in insects feeding on these plants in the wild. Thus, alternative lipases are needed for insect resistance management. The present invention is useful for avoiding the inherent disadvantage of pre-existing natural selection pressure, while conferring numerous other advantages such as low cost relative to repeated-application pesticides and effective insecticidal properties.

SUMMARY OF THE INVENTION

Methods and compositions for creating or enhancing insect resistance in plants are provided. The compositions and methods of the invention may be used in a variety of systems for controlling plant and non-plant pests, including propagating lineages of insect-resistant crops and targeting expression of pesticidal proteins to plant organs that are particularly susceptible to infestation, such as roots and leaves. These methods also find use in insect resistance management.

The methods of the invention comprise introducing into the plant of interest nucleotide sequences that encode non-plant insecticidal lipases, such as non-plant lipid acyl hydrolases. Also included are methods of transformation and regeneration of plants comprising constructs encoding such insecticidal lipases.

The compositions of the invention include nucleotide constructs capable of expressing insecticidal non-plant lipases, such as non-plant lipid acyl hydrolases, in plants. DNA sequences encoding such lipases useful in the practice of the invention are also provided. In some embodiments the DNA sequences are optimized for expression in plants. The DNA sequences encoding these insecticidal lipases can be used to transform plants and other organisms for the control of pests. Transformed microorganisms and transformed plants, plant tissues, and plant cells, and seeds thereof are also provided.

DETAILED DESCRIPTION OF THE INVENTION

Figure 1:
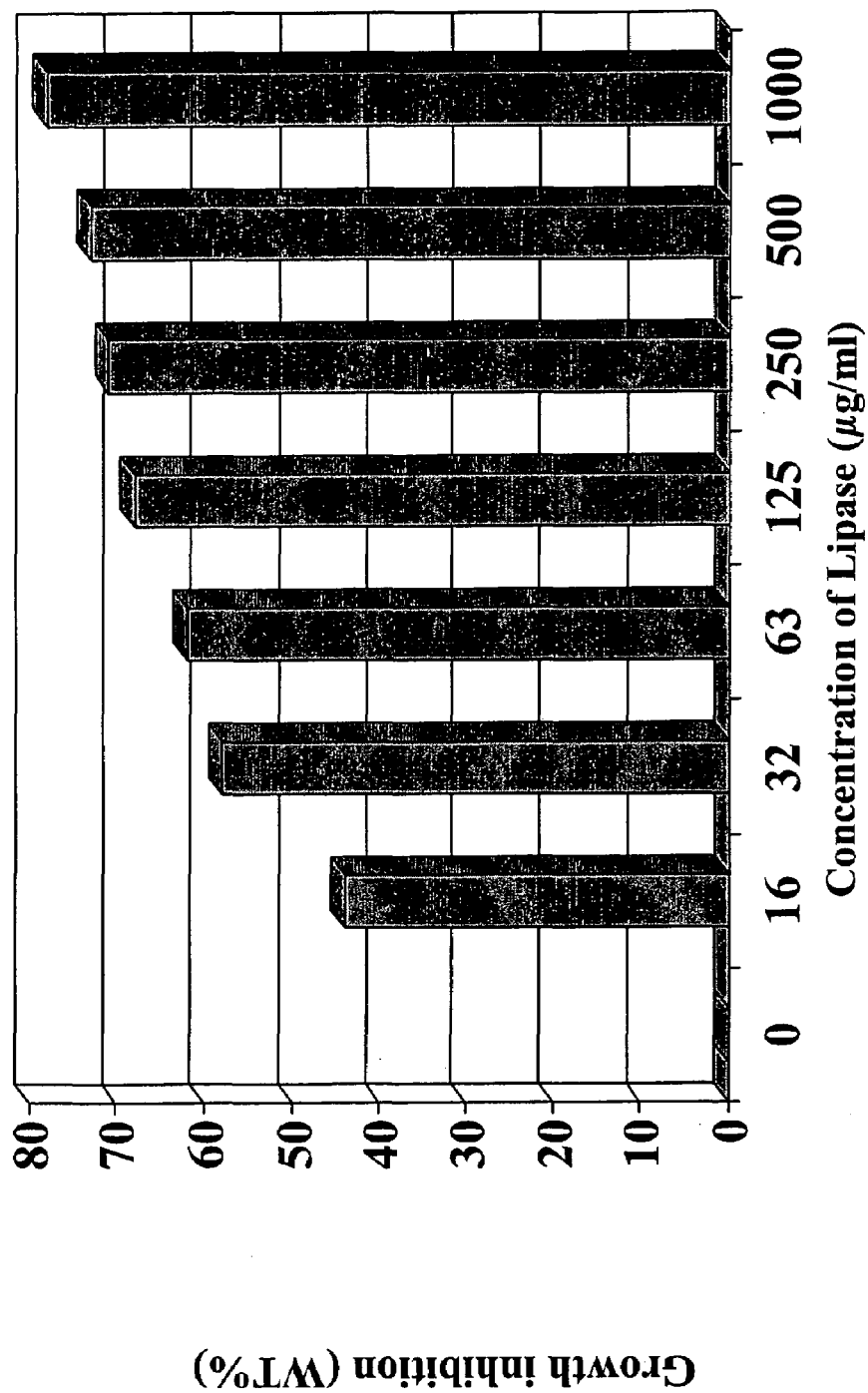
FIG. 1 shows western corn rootworm (WCRW) bioassay results from feeding *Candida cylindracea* lipase (as set forth in SEQ ID NO:2) to developing larvae. The dietary lipase causes a dose-dependent inhibition of larval growth as a percentage of wild-type controls.

The present invention is drawn to methods and compositions for creating and enhancing insect resistance in plants by introducing non-plant transgenes encoding insecticidal lipases. As will be described herein, these methods are useful for conferring insect resistance to a wide variety of plants including crops and other domesticated plant species.

In particular embodiments, the methods comprise introducing a DNA construct encoding an insecticidal lipase, such as a lipid acyl hydrolase, into a plant. Once constructs comprising insecticidal lipases are introduced into the cells of the plant, the encoded lipase is transcribed and translated by the endogenous cellular machinery. When insects attempt to feed or lay eggs in the transgenic plant, the lipases kill the insects or inhibit their growth. Plant cells, organs, seeds and/or the entire plant are thereby made resistant to infestation. Because the cells are stably transformed by these methods, the invention is useful in creating seed and filial lines that are also insect resistant. The methods of the invention further encompass the use of combinations of insecticidal lipases and other pesticides. Such combinations can have additive and/or synergistic effects on resistance of plants to insects.

The compositions of the invention include polynucleotide constructs comprising nucleic acid molecules encoding insecticidal lipases. These constructs include, but are not limited to, expression cassettes wherein the nucleotide sequences encoding the insecticidal lipases are operably linked to a promoter that drives expression in a plant cell. The invention further provides plant cells, plants, and seeds stably transformed with these polynucleotide constructs. The compositions of the invention are useful in protecting a plant from insect pests, and can be utilized to impact insect pests that interact with a plant during one or more phases of the insect life cycle.

Lipases are well known in the art. One class of lipase is the lipid acyl hydrolase, also known as a triacylglycerol acylhydrolase or triacylglycerol lipase (termed EC 3.1.1.3 enzymes under the IUBMB nomenclature system). These enzymes catalyze the hydrolysis reaction: triacylglycerol+ $H_2O$=diacylglycerol+a carboxylate. Lipid acyl hydrolases all share a common, conserved scissile structural region termed the catalytic triad. The catalytic triad consists of a glycine-X amino acid-serine-X amino acid-glycine motif (GxSxG). It has been demonstrated that amino acid substitution in this region abrogates enzymatic activity. Remarkably, the enzymatic action of these lipid acyl hydrolases also correlates with significant insecticidal activity.

Insecticidal lipases useful in practicing some embodiments of the invention include lipid acyl hydrolases that can impact an insect pest such as those lipases derived from non-plant species as discussed herein and known in the art. The term "impact an insect pest" or "impacting an insect pest" is intended to mean the effect of employing any substance or organism to prevent, destroy, repel, or mitigate an insect pest, such as for example insecticidal lipase. Thus, many beneficial properties are conferred on a transgenic plant expressing insecticidal proteins, e.g., lipase having insecticidal activity (hereinafter referred to as "insecticidal lipases").

As used herein, the term "pesticidal activity" is used to refer to activity of an organism or a substance (such as, for example, a protein), whether toxic or inhibitory, that can be measured by, but is not limited to, pest mortality, pest weight loss, pest repellency, pest growth stunting, and other behavioral and physical changes of a pest after feeding and exposure for an appropriate length of time. In this manner, pesticidal activity impacts at least one measurable parameter of pest fitness. Similarly, "insecticidal activity" may be used to refer to "pesticidal activity" when the pest is an insect pest. "Stunting" is intended to mean greater than 50% inhibition of growth as determined by weight. General procedures for monitoring pesticidal activity include addition of the experimental compound or organism to the diet source in an enclosed container. Assays for assessing pesticidal activity are well known in the art. See, e.g., U.S. Pat. Nos. 6,570,005 and 6,339,144; herein incorporated by reference in their entirety. The optimal developmental stage for testing for pesticidal activity is larvae or immature forms of an insect of interest. The insects may be reared in total darkness at from about 20° C. to about 30° C. and from about 30% to about 70% relative humidity. Bioassays may be performed as described in Czapla and Lang (1990) *J. Econ. Entomol.* 83(6):2480–2485. Methods of rearing insect larvae and performing bioassays are well known to one of ordinary skill in the art.

The term "pesticidally effective amount" connotes a quantity of a substance or organism that has pesticidal activity when present in the environment of a pest. For each substance or organism, the pesticidally effective amount is determined empirically for each pest affected in a specific environment. Similarly, an "insecticidally effective amount" may be used to refer to a "pesticidally effective amount" when the pest is an insect pest. "Creating or enhancing insect resistance" is intended to mean the plant genetically modified in accordance with the methods of the present invention has increased resistance to one or more insect pests relative to a plant having a similar genetic component with the exception of the genetic modification described herein. Genetically modified plants of the present invention are capable of expression of at least one insecticidal lipase, such as a lipid acyl hydrolase, which protects a plant from an insect pest while impacting an insect pest of a plant. "Protects a plant from an insect pest" is intended to mean the mitigating or preventing of insect pest-related damage to a plant by, for example, inhibiting the ability of the insect pest to grow, feed, and/or reproduce or by killing the insect pest. As used herein, "impacting an insect pest of a plant" includes, but is not limited to, deterring the insect pest from feeding further on the plant, harming the insect pest by, for example, inhibiting the ability of the insect to grow, feed, and/or reproduce, or killing the insect pest.

The term "insecticidal lipase" is used in its broadest sense and includes, but is not limited to, any member of the family of lipid acyl hydrolases that has toxic or inhibitory effects on insects. Toxic and inhibitory effects of insecticidal lipases include, but are not limited to, stunting of larval growth, killing eggs or larvae, reducing either adult or juvenile feeding on transgenic plants relative to that observed on wild-type, and inducing avoidance behavior in an insect as it relates to feeding, nesting, breeding, combinations thereof, and the like. Thus, as described herein, insect resistance can be conferred to an organism by introducing a nucleotide sequence encoding an insecticidal lipase or applying an insecticidal substance, which includes, but is not limited to, such an insecticidal protein, to an organism (e.g., a plant or plant part thereof). For example, any insecticidal lipase derived from non-plant sources may be used to create or enhance insect resistance in a plant.

Insecticidal lipases encompassed by the invention may have advantageous properties in addition to causing insect mortality or morbidity. One such advantageous property includes, but is not limited to, the inability to induce an allergic response (i.e., hypoallergenic lipid acyl hydrolase). Thus, in some embodiments, the insecticidal lipid acyl hydrolase useful in the invention is further selected based on the inability to induce or exacerbate allergy in a target population. Non-plant insecticidal lipases, such as non-plant lipid acyl hydrolases, including but not limited to those disclosed herein, are less likely to induce or exacerbate allergy. Plants expressing a hypoallergenic insecticidal lipase such as a lipid acyl hydrolase, are thus rendered resistant to infestation without attendant deleterious effects on the feed/food quality. Methods of assessing allergic responses to food are known in art and routinely performed.

Insecticidal lipases encompassed by the invention, such as a lipid acyl hydrolases, find use as an alternative to a previously implemented pesticide method such as pesticide application and/or prior genetic modification of a plant. Measures aimed at reducing the potential for insect pests to become resistant to a pesticide are termed "insect resistance management." Non-plant insecticidal lipases, such as non-plant insecticidal lipid acyl hydrolases, including but not limited to those disclosed herein, are of use in insect resistance management because they are an alternative to current pesticides.

Therefore, the insecticidal lipases, such as lipid acyl hydrolases, that find use in the invention may also be further selected for use in insect resistance management programs. Those of skill in the art recognize that selection of a particular insecticidal lipase, such as a lipid acyl hydrolase, will depend on the type of resistant insect strain that emerges (or is likely to emerge) as well as the crops that are likely to suffer from infestation.

The insecticidal lipases encompassed by the invention include lipid acyl hydrolases having insecticidal activity and which are encoded by nucleic acid sequences from non-plant sources, or fragments and variant sequences thereof "Non-plant" is intended to mean encompassing all of the phylogentic Kingdoms except Planta (i.e., encompassing Kingdom Eubacteria, Kingdom Euryarcheota, Kingdom Crenarcheota, Kingdom Protozoa, Kingdom Mycota, Kingdom Chromista, and Kingdom Animalia).

As one example, insecticidal lipases, such as lipid acyl hydrolases, can be derived from species within the Kingdom Mycota; e.g., Candida lipase 1 (CLIP1) derived from the yeast *Candida cylindracea* (previously known as *Candida rugosa*) (e.g., GenBank Accession No. X16712; and the nucleotide sequence as set forth in SEQ ID NO:1 encoding the amino acid sequence as set forth in SEQ ID NO:2; see also, Longhi et al. (1992) *Biochim. Biophys. Acta* 1131: 227–232, and Lotti et al. (1993) *Gene* 124:45–55); and a *Rhizopus* lipase derived from *Rhizopus arrhizus* (also known as *R. oryzae*) (e.g., GenBank Accession No. AF229435; and the nucleotide sequence as set forth in SEQ ID NO:5, with the nucleotide region 901–2079 encoding the amino acid sequence as set forth in SEQ ID NO:6); and functional variants or fragments thereof As another example, insecticidal lipases, such as lipid acyl hydrolases, can be derived from species within the Kingdom *Eubacteria*; e.g., lipase derived from *Nitrosomonas europaea* (e.g., GenBank Accession No. BX321865; nucleotide region 4475–5422 encoding a protein having GenPept Accession No. CAD86430 and deposited as ATCC Accession No. 19718D, and the nucleotide sequence as set forth in SEQ ID NO:7 encoding the amino acid sequence set forth in SEQ ID NO:8), and functional variants or fragments thereof.

As yet another example, insecticidal lipases, such as lipid acyl hydrolases, can be derived from species within the Kingdom *Animalia*; e.g., lipase derived from porcine pancreas (e.g., the amino acid sequence as set forth in SEQ ID NO:4 as encoded by the maize-optimized coding sequence shown in SEQ ID NO:3), and functional variants or fragments thereof.

Thus, the insecticidal lipases encompassed by the invention, such as lipid acyl hydrolases, may be expressed in a transgenic plant or plant part. For example, in some embodiments, the plant is stably transformed with a nucleotide construct comprising a cassette wherein at least one nucleotide sequence encoding an insecticidal lipase, such as a lipid acyl hydrolase, is operably linked to a promoter that drives expression in a plant cell. In this manner, the expression of insecticidal lipases, such as lipid acyl hydrolases, encompassed by the invention can confer resistance of a plant or plant part to insect infestation. Such an expression cassette can comprise a sequence encoding an insecticidal lipase, such as lipid acyl hydrolase, for example, the sequence set forth in SEQ ID NO: 1 (encoding a fungal insecticidal lipase termed CLIP1 as set forth in SEQ ID NO:2); SEQ ID NO:3 (encoding an animal insecticidal lipase termed porcine pancreatic lipase as set forth in SEQ ID NO:4); SEQ ID NO:5 (encoding a fungal insecticidal lipase derived from *Rhizopus arrhizus* as set forth in SEQ ID NO:6); or SEQ ID NO:7 (encoding a bacterial insecticidal lipase derived from *Nitrosomonas europaea* as set forth in SEQ ID NO:8), or a sequence encoding a functional fragment or variants of an insecticidal lipase, such as the lipase set forth in SEQ ID NO:2, 4, 5, or 8.

Thus, fragments and variants of insecticidal lipase-encoding polynucleotides and proteins encoded thereby also find use in preparing compositions and practicing methods of the present invention. By the term "fragment" is intended a portion of the polynucleotide or a portion of the amino acid sequence and hence protein encoded thereby. Fragments of a polynucleotide may encode protein fragments that retain the biological activity of the native protein and hence retain insecticidal lipase activity. Thus, fragments of a nucleotide sequence may range from at least about 20 nucleotides, about 50 nucleotides, about 100 nucleotides, and up to the full-length polynucleotide encoding the insecticidal lipase of interest.

A fragment of a polynucleotide that encodes a biologically active portion of an insecticidal lipase useful in the invention, such as a lipid acyl hydrolase, will encode at least 15, 25, 30, 50, 100, 150, 200, 250, or 300 contiguous amino acids, or up to the total number of amino acids present in a full-length insecticidal lipase protein (for example, 549 amino acids for SEQ ID NO:2, 450 amino acids for SEQ ID NO:4, 392 amino acids for SEQ ID NO:6, and 314 amino acids for SEQ ID NO:8).

A biologically active portion of an insecticidal lipase, such as a lipid acyl hydrolase, can be prepared by isolating a portion of one of the polynucleotides encoding an insecticidal lipase, expressing the encoded portion of the lipase protein (e.g., by recombinant expression in vitro), and assessing the activity of the expressed portion of the lipase protein for lipid acyl hydrolase activity and/or insecticidal activity. For example, lipid acyl hydrolases retain a conserved amino acid sequence termed the catalytic triad (i.e., GxSxG) as discussed supra. Thus, a fragment of a lipid acyl hydrolase having a catalytic triad finds use in the invention, as it retains enzymatic activity.

Polynucleotides that are fragments of nucleotide sequences encoding insecticidal lipases, such as lipid acyl hydrolases, comprise at least 16, 20, 50, 75, 100, 150, 200, 250, 300, 350, 400, 450, 500, 550, 600, 650, 700, 750, 800, 850, 900, or 940 contiguous nucleotides, or up to the number of nucleotides present in a full-length polynucleotide disclosed herein (for example, 1650 nucleotides for SEQ ID NO:1; 1450 nucleotides for SEQ ID NO:3; 3120 nucleotides, of which 1178 contiguous nucleotides from 901–2079 are coding sequence, for SEQ ID NO:5; and 942 nucleotides for SEQ ID NO:7).

"Variants" is intended to mean substantially similar sequences. For polynucleotides, a variant comprises a polynucleotide having deletions (i.e., truncations) at the 5' and/or 3' end; deletion and/or addition of one or more nucleotides at one or more internal sites in the native polynucleotide; and/or substitution of one or more nucleotides at one or more sites in the native polynucleotide. As used herein, a "native" polynucleotide or polypeptide comprises a naturally occurring nucleotide sequence or amino acid sequence, respectively. For polynucleotides, conservative variants include those sequences that, because of the degeneracy of the genetic code, encode the amino acid sequence of one of the insecticidal lipase polypeptides useful in the invention, such as lipid acyl hydrolases. Naturally occurring variants, such as allelic variants, can be identified with the use of well-known molecular biology techniques, as, for example, with polymerase chain reaction (PCR) and hybridization techniques as outlined below. Variant polynucleotides also include synthetically derived polynucleotides, such as those generated, for example, by using site-directed mutagenesis but which still encode an insecticidal lipase protein useful in the invention, such as an acyl lipid acyl hydrolase. Generally, variants of a particular polynucleotide of the invention will have at least about 40%, 45%, 50%, 55%, 60%, 65%, 70%, 75%, 80%, 85%, 90%, 91%, 92%, 93%, 94%, 95%, 96%, 97%, 98%, 99%, or more sequence identity to that particular polynucleotide as determined by sequence alignment programs and parameters as described elsewhere herein.

Variants of a particular nucleotide sequence encompassed by the invention (i.e., the reference nucleotide sequence) can also be evaluated by comparison of the percent sequence identity between the polypeptide encoded by a variant nucleotide sequence and the polypeptide encoded by the reference nucleotide sequence. Thus, for example, isolated nucleic acids that encode a polypeptide with a given percent sequence identity to the polypeptide of SEQ ID NO:2, 4, 6, or 8 are included. Percent sequence identity between any two polypeptides can be calculated using sequence alignment programs and parameters described elsewhere herein. Where any given pair of polynucleotides of the invention is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99%, or more sequence identity.

"Variant" protein is intended to mean a protein derived from the native protein by deletion (so-called truncation) of one or more amino acids at the N-terminal and/or C-terminal end of the native protein; deletion and/or addition of one or more amino acids at one or more internal sites in the native protein; or substitution of one or more amino acids at one or more sites in the native protein. Variant proteins encompassed by the present invention are biologically active, that is they continue to possess the desired biological activity of the native protein, that is, retaining insecticidal properties and/or lipase activity as described herein. Such variants may result from, for example, genetic polymorphism or from human manipulation. Biologically active variants of insecticidal lipase proteins that are useful in the invention, such as lipid acyl hydrolases, will have at least about 40%, 45%, 50%, 55%, 60%, 65%, 70%, 75%, 80%, 85%, 90%, 91%, 92%, 93%, 94%, 95%, 96%, 97%, 98%, 99%, or more sequence identity to the amino acid sequence for the native protein as determined by sequence alignment programs and parameters described elsewhere herein. A biologically active variant of a protein of the invention may differ from native protein by as few as 1–15 amino acid residues, as few as 1–10, such as 6–10, as few as 5, as few as 4, 3, 2, or even 1 amino acid residue.

The insecticidal lipases of the invention, such as lipid acyl hydrolases, may be altered in various ways including amino acid substitutions, deletions, truncations, and insertions. Methods for such manipulations are generally known in the art. For example, amino acid sequence variants and fragments of insecticidal lipases, such as lipid acyl hydrolase fragments, can be prepared by mutations in the DNA. Methods for mutagenesis and nucleotide sequence alterations are well known in the art. See, for example, Kunkel (1985) *Proc. Natl. Acad Sci. USA* 82:488–492; Kunkel et al. (1987) *Meth. Enzymol.* 154:367–382; U.S. Pat. No. 4,873,192; Walker and Gaastra, eds. (1983) *Techniques in Molecular Biology* (MacMillan Publishing Company, New York), and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

Specifically, those of skill in the art will recognize that regions of the nucleotide sequence or amino acid sequence that are highly conserved in lipid acyl hydrolases as compared to other regions within the sequence, will generally be less tolerant to modification through amino acid substitutions. As such, the previously discussed catalytic triad found in lipid acyl hydrolases, consisting of a glycine-X amino acid-serine-X amino acid-glycine motif (GxSxG), may be preserved in certain embodiments to retain enzymatic and/or biological activity.

Thus, the nucleotide sequences for use in practicing the invention include both the naturally occurring sequences as well as mutant forms. Likewise, the insecticidal proteins of the invention encompass both naturally occurring proteins as well as variations and modified forms thereof Such variants will continue to possess the desired insecticidal activity. Obviously, the mutations that will be made in the DNA encoding the variant must not place the sequence out of reading frame and optimally will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. For example, the activity can be evaluated by a bioassay in which the insecticidal lipase is added to the diet of corn rootworm larvae as described in Example 1. See, for example, Rose and McCabe (1973) *J. Econ. Entomol.* 66:393, herein incorporated by reference in its entirety.

Variant nucleotide sequences and proteins also encompass sequences and proteins derived from a mutagenic and recombinogenic procedure such as DNA shuffling. With such a procedure, one or more different insecticidal lipase sequences can be manipulated to create a new lipase possessing the desired insecticidal properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest, such as the catalytic triad and variants thereof, may be shuffled between nucleotide sequences of the invention, such as SEQ ID NO:1, and other known lipase genes to obtain a new gene coding for a protein with an improved property of interest, such as an increased insecticidal activity. Strategies for DNA shuffling are known in the art. See, for example, Stemmer (1994) *Proc. Natl. Acad. Sci. USA* 91:10747–10751; Stemmer (1994) *Nature* 370:389–391; Crameri et al. (1997) *Nature Biotech.* 15:436–438; Moore et al. (1997) *J. Mol. Biol.* 272:336–347; Zhang et al (1997) *Proc. Natl. Acad. Sci. USA* 94:4504–4509; Crameri et al. (1998) *Nature* 391:288–291; and U.S. Pat. Nos. 5,605,793 and 5,837,458.

As one example, altered substrate specificity could be one parameter for selection of products of gene shuffling. Lipid acyl hydrolases comprise a diverse multigene family that is conserved across many species. The enzymes exhibit hydrolyzing activity for many glyco- and phospholipids. Substrates include monogalactosyldiacylglycerol, acylsterylglucoside, phosphatidylcholine, lysophosphatidylcholine, phosphatidylethanolamine, lysophosphatidylethanolamine, phosphatidylinositol, as well as many other lipid substrates. Similarly, membrane compositions of various insects as well as plants can vary from species to species and can be affected by diet or growth conditions. Consequently, the activity of a given lipid acyl hydrolase for a given substrate could affect both specificity and potency. As another example, altered solubility and protein stability could also be a parameter for selection of products of gene shuffling. Insecticidal lipases, such as lipid acyl hydrolases, are active in the harsh environment of the insect gut lumen. Ingested proteins such as these are digested by proteases, and affected by reducing or oxidizing conditions that vary according to the insect species tested. The solubility and stability of lipid acyl hydrolases both in the transgenic plant and in the insect gut lumen could affect biological activity. For example, the gut pH of corn rootworm is 5.5–6.0. Thus, selection of shuffled gene products for enzymatic activity toward lipid substrates in this pH range is another parameter that could affect toxicity of the protein toward insects. Thus, it is recognized that the sequences disclosed can be used together in shuffling experiments as well as with other insecticidal lipase sequences, particularly other lipid acyl hydrolases, and the like.

Thus, variants of a polypeptide should retain the desired biological activity of the native sequence. Methods are available in the art for determining whether a variant polypeptide retains the desired biological activity of the native polypeptide. Biological activity can be measured using assays specifically designed for measuring activity of the native polypeptide or protein. See, for example, Andrews et al. (1988) *Biochem J* 252:199–206; and U.S. Pat. No. 5,743,477; both of which are herein incorporated by reference in their entirety. Additionally, antibodies raised against the native sequence polypeptide can be tested for their ability to bind to the variant polypeptide, where effective binding is indicative of a polypeptide having a conformation similar to that of the native polypeptide.

The following terms are used to describe the sequence relationships between two or more polynucleotides or polypeptides: (a) “reference sequence”, (b) “comparison window”, (c) “sequence identity”, and, (d) “percentage of sequence identity.”

(a) As used herein, “reference sequence” is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, “comparison window” makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two polynucleotides. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11–17; the local alignment algorithm of Smith et al. (1981) *Adv. Appl. Math.* 2:482; the global alignment algorithm of Needleman and Wunsch (1970) *J. Mol. Biol.* 48:443–453; the search-for-local alignment method of Pearson and Lipman (1988) *Proc. Natl. Acad. Sci.* 85:2444–2448; the algorithm of Karlin and Altschul (1990) *Proc. Natl. Acad. Sci. USA* 87:2264, modified as in Karlin and Altschul (1993) *Proc. Natl. Acad. Sci. USA* 90:5873.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73:237–244 (1988); Higgins et al. (1989) *CABIOS* 5:151–153; Corpet et al. (1988) *Nucleic Acids Res.* 16:10881–90; Huang et al. (1992) *CABIOS* 8:155–65; and Pearson et al. (1994) *Meth. Mol. Biol.* 24:307–331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See www.ncbi.nlm.nih.gov. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By “equivalent program,” it is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) J. Mol. Biol. 48:443–453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65, or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff and Henikoff(1989) *Proc. Natl. Acad. Sci. USA* 89:10915).

(c) As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The coding sequences for insecticidal lipases encompassed by the invention, such as lipid acyl hydrolases, can be provided in expression cassettes for expression in the plant or organism of interest. The cassette may include 5' and 3' regulatory sequences operably linked to a polynucleotide encoding an insecticidal lipase, such as an acyl lipid hydrolase. "Operably linked" is intended to mean a functional linkage between two or more elements. For example, an operable linkage between a polynucleotide of interest and a regulatory sequence (i.e., a promoter) is a functional link that allows for expression of the polynucleotide of interest. Operably linked elements may be contiguous or non-contiguous. When used to refer to the joining of two protein coding regions, by operably linked is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of a polynucleotide that encodes an insecticidal lipase, such as a lipid acyl hydrolase, so that the gene is under the transcriptional regulation of the regulatory regions. The expression cassette may additionally contain selectable marker genes.

The expression cassette will include in the 5'-3' direction of transcription, a transcriptional and translational initiation region (i.e., a promoter), an insecticidal lipase-encoding DNA sequence encompassed by the invention, and a transcriptional and translational termination region (i.e., termination region) functional in plants. The regulatory regions (i.e., promoters, transcriptional regulatory regions, and translational termination regions) and/or the lipase-encoding polynucleotides useful in the invention may be native/analogous to the host cell or to each other. Alternatively, the regulatory regions and/or the lipase-encoding polynucleotides useful in the invention may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. As used herein, a chimeric gene comprises a coding sequence operably linked to a transcription initiation region that is heterologous to the coding sequence.

The termination region may be native with the transcriptional initiation region, may be native with the operably linked lipase-encoding polynucleotides of interest, may be native with the plant host, or may be derived from another source (i.e., foreign or heterologous to the promoter, the insecticidal lipase-encoding polynucleotide of interest, the plant host, or any combination thereof). Convenient termination regions are available from the Ti-plasmid of *A. tumefaciens*, such as the octopine synthase and nopaline synthase termination regions. See also Guerineau et al. (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell* 2:1261–1272; Munroe et al. (1990) *Gene* 91:151–158; Ballas et al. (1989) *Nucleic Acids Res.* 17:7891–7903; and Joshi et al. (1987) *Nucleic Acids Res.* 15:9627–9639.

Where appropriate, the polynucleotides may be optimized for increased expression in the transformed plant. That is, the polynucleotides can be synthesized using plant-preferred codons for improved expression. See, for example, Campbell and Gowri (1990) *Plant Physiol.* 92: 1–11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126–6130); potyvirus leaders, for example, TEV leader (Tobacco Etch Virus) (Gallie et al. (1995) *Gene* 165(2):233–238), and human immunoglobulin heavy-chain binding protein (BiP) (Macejak et al. (1991) *Nature* 353:90–94); untranslated leader from the coat protein mRNA of alfalfa mosaic virus (AMV RNA 4) (Jobling et al. (1987) *Nature* 325:622–625); tobacco mosaic virus leader (TMV) (Gallie et al. (1989) in *Molecular Biology of RNA*, ed. Cech (Liss, N.Y.), pp. 237–256); and maize chlorotic mottle virus leader (MCMV) (Lommel et al. (1991) *Virology* 81:382–385). See also, Della-Cioppa et al. (1987) *Plant Physiol.* 84:965–968.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

Because the sequences encoding insecticidal lipases, such as lipid acyl hydrolases that are of particular use in the invention are non-plant derived, those skilled in the art recognize that the native DNA sequence encoding the insecticidal lipase, such as a lipid acyl hydrolase sequence, may not express properly in plants. Therefore, certain modifications to the DNA sequence may be necessary to ensure proper protein expression and folding. For example, *Candida cylindracea* has unusual codon usage. It translates the codon CTG as a serine instead of the usual leucine as in other organisms, see Kwaguchi et al. (1989) *Nature* 6238: 164–166. As a consequence, if one attempted to express the native DNA sequence in plants, the enzyme would contain leucines instead of serines. In some instances, this substitution might not affect enzymatic activity. However, because the catalytic triad requires a serine in the active site, the serine-to-leucine substitution renders the native-encoded lipase inactive in plants. Thus, replacing the CTG codon with a codon that is read as a serine in plants restores activity. For example, substituting CTG with the codons TCT, TCC, TCA, TCG, AGT, or AGC will cause the plant to translate the correct amino acid—serine—instead of leucine. The DNA sequence set forth in SEQ ID NO: 1, which was derived from *Candida cylindracea*, includes these advantageous substitutions.

A number of promoters can be used in the practice of the invention. The promoters can be selected based on the desired outcome. The nucleic acids can be combined with constitutive, tissue-preferred, or other promoters for expression in plants.

Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810–812); rice actin (McElroy et al. (1990) *Plant Cell* 2:163–171); ubiquitin (Christensen et al. (1989) *Plant Mol. Biol.* 12:619–632 and Christensen et al. (1992) *Plant Mol. Biol.* 18:675–689); pEMU (Last et al. (1991) *Theor. Appl. Genet.* 81:581–588); MAS (Velten et al. (1984) *EMBO J.* 3:2723–2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Generally, it will be beneficial to express the insecticidal protein sequences from an inducible promoter, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245–254; Uknes et al. (1992) *Plant Cell* 4:645–656; and Van Loon (1985) *Plant Mol. Virol.* 4:111–116. See also WO 99/43819, herein incorporated by reference.

Of interest are promoters that are expressed locally at or near the site of pathogen infection. See, for example, Marineau et al. (1987) *Plant Mol. Biol.* 9:335–342; Matton et al. (1989) *Molecular Plant-Microbe Interactions* 2:325–331; Somsisch et al. (1986) *Proc. Natl. Acad. Sci. USA* 83:2427–2430; Somsisch et al. (1988) *Mol. Gen. Genet.* 2:93–98; and Yang (1996) *Proc. Natl. Acad. Sci. USA* 93:14972–14977. See also, Chen et al. (1996) *Plant J.* 10:955–966; Zhang et al. (1994) *Proc. Natl. Acad. Sci. USA* 91:2507–2511; Warner et al. (1993) *Plant J.* 3:191–201; Siebertz et al. (1989) *Plant Cell* 1:961–968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant Path.* 41:189–200).

Additionally, as pathogens find entry into plants through wounds or insect damage, a wound-inducible promoter may be used to drive expression of the insecticidal proteins. Such wound-inducible promoters include potato proteinase inhibitor (pin II) gene (Ryan (1990) *Ann. Rev. Phytopath.* 28:425–449; Duan et al. (1996) *Nature Biotechnology* 14:494–498); wun1 and wun2, U.S. Pat. No. 5,428,148; win1 and win2 (Stanford et al. (1989) *Mol. Gen. Genet.* 215:200–208); systemin (McGurl et al. (1992) *Science* 225: 1570–1573); WIP1 (Rohmeier et al. (1993) *Plant Mol. Biol.* 22:783–792; Eckelkamp et al. (1993) *FEBS Letters* 323: 73–76); MPI gene (Corderok et al. (1994) Plant J. 6(2): 141–150); and the like, herein incorporated by reference.

Chemical-regulated promoters can be used to modulate the expression of an insecticidal protein sequence in a plant through the application of an exogenous chemical regulator.

Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) Proc. Natl. Acad. Sci. USA 88:10421–10425 and McNellis et al. (1998) Plant J. 14(2): 247–257) and tetracycline-inducible and tetracycline-repressible promoters (see, for example, Gatz et al. (1991) Mol. Gen. Genet. 227:229–237, and U.S. Pat. Nos. 5,814,618 and 5,789,156), herein incorporated by reference.

Tissue-preferred promoters can be utilized to target enhanced insecticidal lipase expression within a particular plant tissue. Tissue-preferred promoters include Yamamoto et al. (1997) Plant J. 12(2):255–265; Kawamata et al. (1997) Plant Cell Physiol. 38(7):792–803; Hansen et al. (1997) Mol. Gen. Genet. 254(3):337–343; Russell et al. (1997) Transgenic Res. 6(2):157–168; Rinehart et al. (1996) Plant Physiol. 112(3):1331–1341; Van Camp et al. (1996) Plant Physiol. 112(2):525–535; Canevascini et al. (1996) Plant Physiol. 112(2):513–524; Yamamoto et al. (1994) Plant Cell Physiol. 35(5):773–778; Lam (1994) Results Probl. Cell Differ. 20:181–196; Orozco et al. (1993) Plant Mol. Biol 23(6): 1129–1138; Matsuoka et al. (1993) Proc. Natl. Acad. Sci. USA 90(20):9586–9590; and Guevara-Garcia et al. (1993) Plant J. 4(3):495–505. Such promoters can be modified, if necessary, for weak expression.

Leaf-preferred promoters are known in the art. See, for example, Yamamoto et al. (1997) Plant J. 12(2):255–265; Kwon et al. (1994) Plant Physiol. 105:357–67; Yamamoto et al. (1994) Plant Cell Physiol. 35(5):773–778; Gotor et al. (1993) Plant J. 3:509–18; Orozco et al. (1993) Plant Mol. Biol. 23(6):1129–1138; and Matsuoka et al. (1993) Proc. Natl. Acad. Sci. USA 90(20):9586–9590.

Root-preferred promoters are known and can be selected from the many available from the literature or isolated de novo from various compatible species. See, for example, Hire et al. (1992) Plant Mol. Biol. 20(2):207–218 (soybean root-specific glutamine synthetase gene); Keller and Baumgartner (1991) Plant Cell 3(10): 1051–1061 (root-specific control element in the GRP 1.8 gene of French bean); Sanger et al. (1990) Plant Mol. Biol. 14(3):433–443 (root-specific promoter of the mannopine synthase (MAS) gene of Agrobacterium tumefaciens); and Miao et al. (1991) Plant Cell 3(1): 11–22 (full-length cDNA clone encoding cytosolic glutamine synthetase (GS), which is expressed in roots and root nodules of soybean). See also Bogusz et al. (1990) Plant Cell 2(7):633–641, where two root-specific promoters isolated from hemoglobin genes from the nitrogen-fixing nonlegume Parasponia andersonii and the related non-nitrogen-fixing nonlegume Trema tomentosa are described. The promoters of these genes were linked to a β-glucuronidase reporter gene and introduced into both the nonlegume Nicotiana tabacum and the legume Lotus corniculatus, and in both instances root-specific promoter activity was preserved. Leach and Aoyagi (1991) describe their analysis of the promoters of the highly expressed rolC and rolD root-inducing genes of Agrobacterium rhizogenes (see Plant Science (Limerick) 79(1):69–76). They concluded that enhancer and tissue-preferred DNA determinants are dissociated in those promoters. Teeri et al. (1989) used gene fusion to lacZ to show that the Agrobacterium T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see EMBO J. 8(2): 343–350). The TR1' gene, fused to nptII (neomycin phosphotransferase II) showed similar characteristics. Additional root-preferred promoters include the VfENOD-GRP3 gene promoter (Kuster et al. (1995) Plant Mol. Biol. 29(4): 759–772); and rolB promoter (Capana et al. (1994) Plant Mol. Biol. 25(4):681–691. See also U.S. Pat. Nos. 5,837,876; 5,750,386; 5,633,363; 5,459,252; 5,401,836; 5,110,732; and 5,023,179.

"Seed-preferred" promoters include both "seed-specific" promoters (those promoters active during seed development such as promoters of seed storage proteins) as well as "seed-germinating" promoters (those promoters active during seed germination). See Thompson et al. (1989) BioEssays 10: 108, herein incorporated by reference. Such seed-preferred promoters include, but are not limited to, Cim1 (cytokinin-induced message); cZ19B1 (maize 19 kDa zein); milps (myo-inositol-1-phosphate synthase) (see WO 00/11177 and U.S. Pat. No. 6,225,529; herein incorporated by reference). Gamma-zein is an endosperm-specific promoter. Globulin 1 (Glb-1) is a representative embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, gamma-zein, waxy, shrunken 1, shrunken 2, Globulin 1, etc. See also WO 00/12733, where seed-preferred promoters from end1 and end2 genes are disclosed; herein incorporated by reference.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP) (Su et al. (2004) Biotechnol Bioeng. 85:610–9 and Fetter et al. (2004) Plant Cell 16:215–28), cyan fluorescent protein (CYP) (Bolte et al. (2004) J. Cell Science 117:943–54 and Kato et al. (2002) Plant Physiol. 129:913–42), and yellow fluorescent protein (PhiYFP™ from Evrogen; see, Bolte et al. (2004) J. Cell Science 117:943–54). For additional selectable markers, see generally, Yarranton (1992) Curr. Opin. Biotech. 3:506–511; Christopherson et al. (1992) Proc. Natl. Acad Sci. USA 89:6314–6318; Yao et al. (1992) Cell 71:63–72; Reznikoff (1992) Mol. Microbiol. 6:2419–2422; Barkley et al. (1980) in The Operon, pp. 177–220; Hu et al. (1987) Cell 48:555–566; Brown et al. (1987) Cell 49:603–612; Figge et al. (1988) Cell 52:713–722; Deuschle et al. (1989) Proc. Natl. Acad. Aci. USA 86:5400–5404; Fuerst et al. (1989) Proc. Natl. Acad. Sci. USA 86:2549–2553; Deuschle et al. (1990) Science 248:480–483; Gossen (1993) Ph.D. Thesis, University of Heidelberg; Reines et al. (1993) Proc. Natl. Acad. Sci. USA 90:1917–1921; Labow et al. (1990) Mol. Cell. Biol. 10:3343–3356; Zambretti et al. (1992) Proc. Natl.

*Acad Sci. USA* 89:3952–3956; Baim et al. (1991) *Proc. Natl. Acad Sci. USA* 88:5072–5076; Wyborski et al. (1991) *Nucleic Acids Res.* 19:4647–4653; Hillenand-Wissman (1989) *Topics Mol. Struc. Biol.* 10: 143–162; Degenkolb et al. (1991) *Antimicrob. Agents Chemother.* 35:1591–1595; Kleinschnidt et al. (1988) *Biochemistry* 27:1094–1104; Bonin (1993) Ph.D. Thesis, University of Heidelberg; Gossen et al. (1992) *Proc. Natl. Acad Sci. USA* 89:5547–5551; Oliva et al. (1992) *Antimicrob. Agents Chemother.* 36:913–919; Hlavka et al. (1985) *Handbook of Experimental Pharmacology*, Vol. 78 (Springer-Verlag, Berlin); Gill et al. (1988) *Nature* 334:721–724. Such disclosures are herein incorporated by reference.

The above list of selectable marker genes is not meant to be limiting. Any selectable marker gene can be used in the present invention.

The methods of the invention involve introducing a polypeptide or polynucleotide into a plant. "Introducing" is intended to mean presenting to the plant the polynucleotide or polypeptide in such a manner that the sequence gains access to the interior of a cell of the plant. The methods of the invention do not depend on a particular method for introducing a sequence into a plant, only that the polynucleotide or polypeptide gains access to the interior of at least one cell of the plant. Methods for introducing polynucleotides or polypeptides into plants are known in the art including, but not limited to, stable transformation methods, transient transformation methods, and virus-mediated methods.

"Stable transformation" is intended to mean that the nucleotide construct introduced into a plant integrates into the genome of the plant and is capable of being inherited by the progeny thereof. "Transient transformation" is intended to mean that a polynucleotide is introduced into the plant and does not integrate into the genome of the plant or a polypeptide is introduced into a plant.

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway et al. (1986) *Biotechniques* 4:320–334), electroporation (Riggs et al. (1986) *Proc. Natl. Acad. Sci. USA* 83:5602–5606, *Agrobacterium*-mediated transformation (U.S. Pat. No. 5,563,055 and U.S. Pat. No. 5,981,840), direct gene transfer (Paszkowski et al. (1984) *EMBO J.* 3:2717–2722), and ballistic particle acceleration (see, for example, U.S. Pat. Nos. 4,945,050; U.S. Pat. No. 5,879,918; U.S. Pat. Nos. 5,886,244; and, 5,932,782; Tomes et al. (1995) in *Plant Cell, Tissue, and Organ Culture: Fundamental Methods*, ed. Gamborg and Phillips (Springer-Verlag, Berlin); McCabe et al. (1988) *Biotechnology* 6:923–926); and Lec1 transformation (WO 00/28058). Also see Weissinger et al. (1988) *Ann. Rev. Genet.* 22:421–477; Sanford et al. (1987) *Particulate Science and Technology* 5:27–37 (onion); Christou et al. (1988) *Plant Physiol.* 87:671–674 (soybean); McCabe et al. (1988) *Bio/Technology* 6:923–926 (soybean); Finer and McMullen (1991) *In Vitro Cell Dev. Biol.* 27P:175–182 (soybean); Singh et al. (1998) *Theor. Appl. Genet* 96:319–324 (soybean); Datta et al. (1990) *Biotechnology* 8:736–740 (rice); Klein et al. (1988) *Proc. Natl. Acad. Sci. USA* 85:4305–4309 (maize); Klein et al. (1988) *Biotechnology* 6:559–563 (maize); U.S. Pat. Nos. 5,240,855; 5,322,783; and, 5,324,646; Klein et al. (1988) *Plant Physiol.* 91:440–444 (maize); Fromm et al. (1990) *Biotechnology* 8:833–839 (maize); Hooykaas-Van Slogteren et al. (1984) *Nature* (London) 311:763–764; U.S. Pat. No. 5,736,369 (cereals); Bytebier et al. (1987) *Proc. Natl. Acad. Sci. USA* 84:5345–5349 (Liliaceae); De Wet et al. (1985) in *The Experimental Manipulation of Ovule Tissues*, ed. Chapman et al. (Longman, N.Y.), pp. 197–209 (pollen); Kaeppler et al. (1990) *Plant Cell Reports* 9:415–418 and Kaeppler et al. (1992) *Theor. Appl. Genet.* 84:560–566 (whisker-mediated transformation); D'Halluin et al. (1992) *Plant Cell* 4:1495–1505 (electroporation); Li et al. (1993) *Plant Cell Reports* 12:250–255 and Christou and Ford (1995) *Annals of Botany* 75:407–413 (rice); Osjoda et al. (1996) *Nature Biotechnology* 14:745–750 (maize via *Agrobacterium tumefaciens*); all of which are herein incorporated by reference.

In specific embodiments, the insecticidal lipase sequences useful in the invention, such as lipid acyl hydrolases, can be provided to a plant using a variety of transient transformation methods. Such transient transformation methods include, but are not limited to, the introduction of insecticidal lipase proteins, such as lipid acyl hydrolases, or variants and fragments thereof directly into the plant or the introduction of an insecticidal lipase-encoding transcript into the plant. Such methods include, for example, microinjection or particle bombardment. See, for example, Crossway et al. (1986) *Mol Gen. Genet.* 202:179–185; Nomura et al. (1986) *Plant Sci.* 44:53–58; Hepler et al. (1994) *Proc. Natl. Acad. Sci.* 91: 2176–2180 and Hush et al. (1994) *J. Cell Sci.* 107:775–784, all of which are herein incorporated by reference. Alternatively, an insecticidal lipase-encoding polynucleotide can be transiently transformed into the plant using techniques known in the art. Such techniques include viral vector system and the precipitation of the polynucleotide in a manner that precludes subsequent release of the DNA. Thus, the transcription from the particle-bound DNA can occur, but the frequency with which its released to become integrated into the genome is greatly reduced. Such methods include the use particles coated with polyethylimine (PEI; Sigma #P3143).

In other embodiments, the polynucleotide of the invention may be introduced into plants by contacting plants with a virus or viral nucleic acids. Generally, such methods involve incorporating a nucleotide construct of the invention within a viral DNA or RNA molecule. It is recognized that an insecticidal lipase useful in the invention, such as a lipid acyl hydrolase, may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209–221; herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO 99/25821, WO 99/25854, WO 99/25840, WO 99/25855, and WO 99/25853, all of which are herein incorporated by reference. Briefly, the polynucleotide of the invention can be contained in a transfer cassette flanked by two non-recombinogenic recombination sites. The transfer cassette is introduced into a plant having stably incorporated into its genome a target site that is flanked by two non-recombinogenic recombination sites that correspond to the sites of the transfer cassette.

An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick et al. (1986) *Plant Cell Reports* 5:81–84. These plants may then be grown, and either pollinated with the same transformed strain or different strains, and the resulting progeny having expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a polynucleotide of the invention, for example, an expression cassette of the invention, stably incorporated into their genome.

The invention disclosed herein is drawn to compositions and methods for inducing resistance in a plant to plant pests, especially insect pests. Accordingly, the compositions and methods are useful in protecting plants against infestation and associated disease.

Insect pests include insects selected from the orders Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, Trichoptera, etc., particularly Coleoptera and Lepidoptera. Insect pests of particular relevance include those that infest the major crops. For example: Maize: *Ostrinia nubilalis*, European corn borer; *Agrotis ipsilon*, black cutworm; *Helicoverpa zea*, corn earworm; *Spodoptera frugiperda*, fall armyworm; *Diatraea grandiosella*, southwestern corn borer; *Elasmopalpus lignosellus*, lesser cornstalk borer; *Diatraea saccharalis*, surgarcane borer; *Diabrotica virgifera*, western corn rootworm; *Diabrotica longicornis barberi*, northern corn rootworm; *Diabrotica undecimpunctata howardi*, southern corn rootworm; *Melanotus* spp., wireworms; *Cyclocephala borealis*, northern masked chafer (white grub); *Cyclocephala immaculata*, southern masked chafer (white grub); *Popillia japonica*, Japanese beetle; *Chaetocnema pulicaria*, corn flea beetle; *Sphenophorus maidis*, maize billbug; *Rhopalosiphum maidis*, corn leaf aphid; *Anuraphis maidiradicis*, corn root aphid; *Blissus leucopterus leucopterus*, chinch bug; *Melanoplus femurrubrum*, redlegged grasshopper; *Melanoplus sanguinipes*, migratory grasshopper; *Hylemya platura*, seedcorn maggot; *Agromyza parvicornis*, corn blot leafminer; *Anaphothrips obscrurus*, grass thrips; *Solenopsis milesta*, thief ant; *Tetranychus urticae*, twospotted spider mite; Sorghum: *Chilo partellus*, sorghum borer; *Spodoptera frugiperda*, fall armyworm; *Helicoverpa zea*, corn earworm; *Elasmopalpus lignosellus*, lesser cornstalk borer; *Feltia subterranea*, granulate cutworm; *Phyllophaga crinita*, white grub; *Eleodes, Conoderus*, and *Aeolus* spp., wireworms; *Oulema melanopus*, cereal leaf beetle; *Chaetocnema pulicaria*, corn flea beetle; *Sphenophorus maidis*, maize billbug; *Rhopalosiphum maidis*; corn leaf aphid; *Sipha flava*, yellow sugarcane aphid; *Blissus leucopterus leucopterus*, chinch bug; *Contarinia sorghicola*, sorghum midge; *Tetranychus cinnabarinus*, carmine spider mite; *Tetranychus urticae*, twospotted spider mite; Wheat: *Pseudaletia unipunctata*, army worm; *Spodoptera frugiperda*, fall armyworm; *Elasmopalpus lignosellus*, lesser cornstalk borer; *Agrotis orthogonia*, western cutworm; *Elasmopalpus lignosellus*, lesser cornstalk borer; *Oulema melanopus*, cereal leaf beetle; *Hypera punctata*, clover leaf weevil; *Diabrotica undecimpunctata howardi*, southern corn rootworm; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; *Hylemya coarctata*, wheat bulb fly; *Frankliniella fusca*, tobacco thrips; *Cephus cinctus*, wheat stem sawfly; *Aceria tulipae*, wheat curl mite; Sunflower: *Suleima helianthana*, sunflower bud moth; *Homoeosoma electellum*, sunflower moth; *zygogramma exclamationis*, sunflower beetle; *Bothyrus gibbosus*, carrot beetle; *Neolasioptera murtfeldtiana*, sunflower seed midge; Cotton: *Heliothis virescens*, cotton budworm; *Helicoverpa zea*, cotton bollworm; *Spodoptera exigua*, beet armyworm; *Pectinophora gossypiella*, pink bollworm; *Anthonomus grandis*, boll weevil; *Aphis gossypii*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper; *Melanoplus differentialis*, differential grasshopper; *Thrips tabaci*, onion thrips; *Franklinkiella fusca*, tobacco thrips; *Tetranychus cinnabarinus*, carmine spider mite; *Tetranychus urticae*, twospotted spider mite; Rice: *Diatraea saccharalis*, sugarcane borer; *Spodoptera frugiperda*, fall armyworm; *Helicoverpa zea*, corn earworm; *Colaspis brunnea*, grape colaspis; *Lissorhoptrus oryzophilus*, rice water weevil; *Sitophilus oryzae*, rice weevil; *Nephotettix nigropictus*, rice leafhopper; *Blissus leucopterus leucopterus*, chinch bug; *Acrosternum hilare*, green stink bug; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis ipsilon*, black cutworm; *Spodoptera exigua*, beet armyworm; *Heliothis virescens*, cotton budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean thrips; *Thrips tabaci*, onion thrips; *Tetranychus turkestani*, strawberry spider mite; *Tetranychus urticae*, twospotted spider mite; Barley: *Ostrinia nubilalis*, European corn borer; *Agrotis ipsilon*, black cutworm; *Schizaphis graminum*, greenbug; *Blissus leucopterus leucopterus*, chinch bug; *Acrosternum hilare*, green stink bug; *Euschistus servus*, brown stink bug; *Delia platura*, seedcorn maggot; *Mayetiola destructor*, Hessian fly; *Petrobia latens*, brown wheat mite; Oil Seed Rape: *Brevicoryne brassicae*, cabbage aphid; *Phyllotreta cruciferae*, Flea beetle; *Mamestra configurata*, Bertha armyworm; *Plutella xylostella*, Diamond-back moth; *Delia* ssp., Root maggots.

As used herein, the term "plant" includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides.

Nucleotide sequences encoding insecticidal lipases, such as lipid acyl hydrolases, can be manipulated and used to express the proteins in a variety of hosts including, but not limited to, microorganisms and plants. Further, the present invention may be used for transformation of any plant species of interest, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). In specific embodiments, plants of the present invention are crop plants (for example, corn, alfalfa, sunflower, *Brassica*, soybean, cotton, safflower, peanut, sorghum, wheat, millet, tobacco, etc.). In other embodiments, corn and soybean plants are optimal, and in yet other embodiments corn plants are optimal.

Other plants of interest include grain plants that provide seeds of interest, oil-seed plants, such as oleaginous plants, and leguminous plants. Seeds of interest include grain seeds, such as corn, wheat, barley, rice, sorghum, rye, etc. Oil-seed plants include cotton, soybean, safflower, sunflower, Brassica, maize, alfalfa, palm, coconut, etc. "Non-oleaginous plant" is intended to mean any plant except one selected from the group consisting of rapeseed, sunflower, soya, olive tree, and kale. Leguminous plants include beans and peas. Beans include guar, locust bean, fenugreek, soybean, garden beans, cowpea, mungbean, lima bean, fava bean, lentils, chickpea, etc.

In certain embodiments, the polynucleotides encompassed by the present invention can be stacked with any combination of polynucleotide sequences of interest in order to create plants with a desired trait. A trait, as used herein, refers to the phenotype derived from a particular expressed nucleotide sequence or groups of sequences.

In certain embodiments, the polynucleotides of the present invention can be stacked with any combination of polynucleotide sequences of interest in order to create plants with a desired trait. A trait, as used herein, refers to the phenotype derived from a particular sequence or groups of sequences. For example, the polynucleotides of the present invention may be stacked with any other polynucleotides encoding polypeptides having pesticidal and/or insecticidal activity, such as other *Bacillus thuringiensis* toxic proteins (described in U.S. Pat. Nos. 5,366,892; 5,747,450; 5,737,514; 5,723,756; 5,593,881; and Geiser et al. (1986) *Gene* 48:109), lectins (Van Damme et al. (1994) *Plant Mol. Biol.* 24:825, pentin (described in U.S. Pat. No. 5,981,722), and the like. The combinations generated can also include multiple copies of any one of the polynucleotides of interest.

The polynucleotides of the present invention can also be stacked with any other gene or combination of genes to produce plants with a variety of desired trait combinations including, but not limited to, traits desirable for animal feed such as high oil genes (e.g., U.S. Pat. No. 6,232,529); balanced amino acids (e.g., hordothionins (U.S. Pat. Nos. 5,990,389; 5,885,801; 5,885,802; and 5,703,409); barley high lysine (Williamson et al. (1987) *Eur. J. Biochem.* 165:99–106; and WO 98/20122) and high methionine proteins (Pedersen et al. (1986) *J. Biol. Chem.* 261:6279; Kirihara et al. (1988) *Gene* 71:359; and Musumura et al. (1989) *Plant Mol. Biol.* 12:123)); increased digestibility (e.g., modified storage proteins (U.S. application Ser. No. 10/053,410, filed Nov. 7, 2001); and thioredoxins (U.S. application Ser. No. 10/005,429, filed Dec. 3, 2001)); the disclosures of which are herein incorporated by reference.

The polynucleotides of the present invention can also be stacked with traits desirable for disease or herbicide resistance (e.g., fumonisin detoxification genes (U.S. Pat. No. 5,792,931); avirulence and disease resistance genes (Jones et al. (1994) *Science* 266:789; Martin et al. (1993) *Science* 262:1432; Mindrinos et al. (1994) *Cell* 78:1089); acetolactate synthase (ALS) mutants that lead to herbicide resistance such as the S4 and/or Hra mutations; genes coding for resistance to herbicides that act to inhibit action of glutamine synthase, such as phosphinothricin or basta (e.g., bar gene); genes coding for glyphosate resistance (for example, the EPSPS gene and the GAT gene; see, for example, U.S. Publication No. 20040082770 and WO 03/092360)); and traits desirable for processing or process products such as high oil (e.g., U.S. Pat. No. 6,232,529 ); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) *J. Bacteriol.* 170:5837–5847) facilitate expression of polyhydroxyalkanoates (PHAs)); the disclosures of which are herein incorporated by reference. One could also combine the polynucleotides of the present invention with polynucleotides providing agronomic traits such as male sterility (e.g., see U.S. Pat. No. 5,583,210), stalk strength, flowering time, or transformation technology traits such as cell cycle regulation or gene targeting (e.g., WO 99/61619, WO 00/17364, and WO 99/25821); the disclosures of which are herein incorporated by reference.

These stacked combinations can be created by any method including, but not limited to, cross-breeding plants by any conventional or TopCross methodology, or genetic transformation. If the sequences are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO 99/25821, WO 99/25854, WO 99/25840, WO 99/25855, and WO 99/25853, all of which are herein incorporated by reference.

The compositions and methods of the invention may be used for protecting agricultural crops and products from pests by introduction of insecticidal lipase encoding sequences, such as those encoding lipid acyl hydrolases, via a suitable vector into a microbial host, and then applying the host to the environment or plants. While the invention does not depend on a particular biological mechanism for increasing the resistance of a plant to an insect, a transformed organism may comprise plant and insect cells, bacteria, yeast, virus, such as baculoviruses, protozoa, nematodes and algae, comprising a DNA molecule of the invention, an expression cassette comprising the said DNA molecule, or a vector molecule comprising the said expression cassette, optimally stably incorporated into the genome of the transformed organism. Microorganism hosts may be selected which are known to occupy the "phytosphere" (phylloplane, phyllosphere, rhizosphere, and/or rhizoplana) of one or more crops of interest. These microorganisms are selected so as to be capable of successfully competing in the particular environment with the wild-type microorganisms, provide for stable maintenance and expression of the gene expressing the insecticidal lipase, and, desirably, provide for improved protection of the insecticidal lipase from environmental degradation and inactivation.

Microorganisms of interest include bacteria, algae, and fungi. Of particular interest are microorganisms, such as bacteria, e.g., *Pseudomonas, Erwinia, Serratia, Klebsiella, Xanthomonas, Streptomyces, Rhizobium, Rhodopseudomonas, Methylius, Agrobacterium, Acetobacter, Lactobacillus, Arthrobacter, Azotobacter, Leuconostoc,* and *Alcaligenes*, fungi, particularly yeast, e.g., *Saccharomyces, Cryptococcus, Kluyveromyces, Sporobolomyces, Rhodotorula,* and *Aureobasidium*. Of particular interest are such phytosphere bacterial species as *Pseudomonas syringae, Pseudomonas fluorescens, Serratia marcescens, Acetobacter xylinum, Agrobacteria, Rhodopseudomonas spheroides, Xanthomonas campestris, Rhizobium melioti, Alcaligenes entrophus, Clavibacter xyli* and *Azotobacter vinlandir*, and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces rosues, S. odorus, Kluyveromyces veronae,* and *Aureobasidium pollulans*. Of particular interest are the pigmented microorganisms.

A number of ways are available for introducing a gene expressing an insecticidal lipase, such as a lipid acyl hydrolase, into the microorganism host under conditions that allow for stable maintenance and expression of the gene. For example, expression cassettes can be constructed which include the nucleotide constructs of interest operably linked with the transcriptional and translational regulatory signals for expression of the nucleotide constructs, and a nucleotide sequence homologous with a sequence in the host organism, whereby integration will occur, and/or a replication system that is functional in the host, whereby integration or stable maintenance will occur.

Transcriptional and translational regulatory signals include, but are not limited to, promoters, transcriptional initiation start sites, operators, enhancers, other regulatory elements, ribosomal binding sites, an initiation codon, termination signals, and the like. See, for example, U.S. Pat. No. 5,039,523; U.S. Pat. No. 4,853,331; EPO 0480762A2; Sambrook et al., eds. (2000) *Molecular Cloning: A Laboratory Manual* ($3^{rd}$ ed.; Cold Spring Harbor Laboratory Press, Plainview, N.Y.); Davis et al., eds. (1980) *Advanced Bacterial Genetics* (Cold Spring Harbor Laboratory, Cold Spring Harbor, N.Y.; and the references cited therein.

Suitable host cells may include either prokaryotes or eukaryotes, where the insecticidal lipase-containing cells will be treated to prolong the activity of the enzyme, Usually the treated cell is applied to the environment of the target pest(s), where the cells do not produce substances toxic to higher organisms, such as mammals. However, organisms that produce substances toxic to higher organisms could be used, where the toxin is unstable or the level of application sufficiently low as to avoid any possibility of toxicity to a mammalian host. Hosts of particular interest will be prokaryotes and lower eukaryotes, such as fungi. Illustrative prokaryotes, both gram-negative and gram-positive, include *Enterobacteriaceae*, such as *Escherichia, Erwinia, Shigella, Salmonella*, and *Proteus; Bacillaceae; Rhizobiceae*, such as *Rhizobium; Spirillaceae*, such as photobacterium, *Zymomonas, Serratia, Aeromonas, Vibrio, Desulfovibrio, Spirillum; Lactobacillaceae; Pseudomonadaceae*, such as *Pseudomonas* and *Acetobacter; Azotobacteraceae* and *Nitrobacteraceae*. Among eukaryotes are fungi, such as *Phycomycetes* and *Ascomycetes*, which includes yeast, such as *Saccharomyces* and *Schizosaccharromyces*; and *Basidiomycetes* yeast, such as *Rhodotorula, Aureobasidium, Sporobolomyces*, and the like.

Characteristics of particular interest in selecting a host cell for purposes of production include ease of introducing the insecticidal lipase coding sequence, such as a lipid acyl hydrolase coding sequence, into the host, availability of expression systems, efficiency of expression, stability of the protein in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; leaf affinity; lack of mammalian toxicity; attractiveness to pests for ingestion; ease of killing and fixing without damage to the toxin; and the like. Other considerations include ease of formulation and handling, economics, storage stability, and the like.

Host organisms of particular interest include yeast, such as *Rhodotorula* sp., *Aureobasidium* sp., *Saccharomyces* sp., and *Sporobolomyces* sp., phylloplane organisms such as *Pseudomonas* sp., *Erwinia* Sp., and *Flavobacterium* sp., or such other organisms including *Pseudomonas aeruginosa, Pseudomonas fluorescens, Saccharomyces cerevisiae, Bacillus thuringiensis, Escherichia coli, Bacillus subtilis*, and the like.

Sequences encoding the insecticidal lipases, such as lipid acyl hydrolases, encompassed by the invention can be introduced into microorganisms that multiply on plants (epiphytes) to deliver insecticidal lipases, such as lipid acyl hydrolases, to potential target pests. Epiphytes, for example, can be gram-positive or gram-negative bacteria.

Root-colonizing bacteria, for example, can be isolated from the plant of interest by methods known in the art. Specifically, a *Bacillus cereus* strain that colonizes roots could be isolated from roots of a plant (see, for example, Handelsman et al. (1991) *Appl. Environ. Microbiol.* 56:713–718). Sequences encoding insecticidal lipases, such as lipid acyl hydrolases, encompassed by the invention, could be introduced into a root-colonizing *Bacillus cereus* by standard methods known in the art.

Sequences encoding insecticidal lipases, such as lipid acyl hydrolases, can be introduced, for example, into the root-colonizing *Bacillus* by means of electro-transformation. Specifically, sequences encoding the insecticidal lipases, such as lipid acyl hydrolases, can be cloned into a shuttle vector, for example, pHT3101 and the shuttle vector can be transformed into the root-colonizing *Bacillus* by means of electroporation (Lerecius et al. (1989) *FEMS Microbiol. Letts.* 60:211–218).

Expression systems can be designed so that insecticidal lipases, such as lipid acyl hydrolases, are secreted outside the cytoplasm of gram-negative bacteria, *E. coli*, for example. Advantages of having insecticidal lipases, such as lipid acyl hydrolases, secreted are: (1) avoidance of potential cytotoxic effects of the protein that is expressed, and (2) improvement in the efficiency of purification of the protein that is expressed, including, but not limited to, increased efficiency in the recovery and purification of the protein per volume cell broth and decreased time and/or costs of recovery and purification per unit protein.

Insecticidal lipases, such as lipid acyl hydrolases, can be made to be secreted in *E. coli*, for example, by fusing an appropriate *E. coli* signal peptide to the amino-terminal end of the insecticidal lipase. Signal peptides recognized by *E. coli* can be found in proteins already known to be secreted in *E. coli*, for example the OmpA protein (Ghrayeb et al. (1984) *EMBO J.*, 3:2437–2442). OmpA is a major protein of the *E. coli* outer membrane, and thus its signal peptide is thought to be efficient in the translocation process. Also, the OmpA signal peptide does not need to be modified before processing as may be the case for other signal peptides, for example lipoprotein signal peptide (Duffaud et al. (1987) *Meth. Enzymol.* 153:492).

Insecticidal lipases encompassed by the invention, such as lipid acyl hydrolases, can be fermented in a bacterial host and the resulting bacteria processed and used as a microbial spray in the same manner that *Bacillus thuringiensis* strains have been used as insecticidal sprays. In the case of insecticidal lipases, such as lipid acyl hydrolases, which can be secreted from *Bacillus*, the secretion signal is removed or mutated using procedures known in the art. Such mutations and/or deletions prevent secretion of the insecticidal lipases into the growth medium during the fermentation process. The insecticidal lipases, such as lipid acyl hydrolases, are retained within the cells and the cells are then processed to yield the encapsulated insecticidal lipases, such as lipid acyl hydrolases. Any suitable microorganism can be used for this purpose. *Pseudomonas* has been used to express *Bacillus thuringiensis* endotoxins as encapsulated proteins and the resulting cells processed and sprayed as an insecticide. See, for example, Gaertner et al. (1993), in *Advanced Engineered Pesticides*, ed. L. Kim (Marcel Decker, Inc.).

Alternatively, insecticidal lipases, such as lipid acyl hydrolases, are produced by introducing a heterologous gene into a cellular host. Expression of the heterologous gene results, directly or indirectly, in the intracellular production and maintenance of the pesticide. These cells are then treated under conditions that prolong the activity of the toxin produced in the cell when the cell is applied to the environment of target pest(s). The resulting product retains the toxicity of the toxin. These naturally encapsulated insecticidal lipases, such as lipid acyl hydrolases, may then be formulated in accordance with conventional techniques for application to the environment hosting a target pest, e.g., soil, water, and foliage of plants. See, for example EPA 0192319, and the references cited therein.

When insecticidal lipases are expressed in a host organism, any portion of the organism may be used prepare an insecticidal composition. Thus, formulations may include: a transformed microorganism, whether whole organisms, tissues, cells, spore(s); insecticidal component(s), pest-impacting component(s), mutant(s); living or dead cells and cell components, including mixtures of living and dead cells and cell components, and including broken cells and cell components, or an isolated enzyme. Further, additional components can be added to the insecticidal compositions such as carriers that can form, for example, a suspension, a solution, an emulsion, a dusting powder, a dispersible granule, a wettable powder, and an emulsifiable concentrate, an aerosol, an impregnated granule, an adjuvant, a coatable paste, and also encapsulations in, for example, polymer substances.

Such compositions disclosed above may be obtained by the addition of a surface-active agent, an inert carrier, a preservative, a humectant, a feeding stimulant, an attractant, an encapsulating agent, a binder, an emulsifier, a dye, a U.V. protectant, a buffer, a flow agent or fertilizers, micronutrient donors or other preparations that influence plant growth. One or more agrochemicals including, but not limited to, herbicides, insecticides, fungicides, bactericides, nematocides, molluscicides, acaracides, plant growth regulators, harvest aids and fertilizers, can be combined with carriers, surfactants or adjuvants customarily employed in the art of formulation or other components to facilitate product handling and application for particular target pests. Suitable carriers and adjuvants can be solid or liquid and correspond to the substances ordinarily employed in formulation technology, e.g., natural or regenerated mineral substances, solvents, dispersants, wetting agents, tackifiers, binders, or fertilizers.

The active ingredients of the present invention are normally applied in the form of compositions and can be applied to the crop area or plant to be treated, simultaneously or in succession, with other compounds. Methods of applying an active ingredient of the present invention or an agrochemical composition of the present invention that contains at least one of the insecticidal lipases, such as lipid acyl hydrolases, produced by the bacterial strains encompassed by the present invention include, but are not limited to, foliar application, seed coating, and soil application. The number of applications and the rate of application depend on the intensity of infestation by the corresponding pest.

Suitable surface-active agents include, but are not limited to, anionic compounds such as a carboxylate of, for example, a metal; carboxylate of a long chain fatty acid; an N-acylsarcosinate; mono- or di-esters of phosphoric acid with fatty alcohol ethoxylates or salts of such esters; fatty alcohol sulfates such as sodium dodecyl sulfate, sodium octadecyl sulfate, or sodium cetyl sulfate; ethoxylated fatty alcohol sulfates; ethoxylated alkylphenol sulfates; lignin sulfonates; petroleum sulfonates; alkyl aryl sulfonates such as alkyl-benzene sulfonates or lower alkylnaphtalene sulfonates, e.g., butyl-naphthalene sulfonate; salts of sulfonated naphthalene-formaldehyde condensates; salts of sulfonated phenol-formaldehyde condensates; more complex sulfonates such as the amide sulfonates, e.g. the sulfonated condensation product of oleic acid and N-methyl taurine; or the dialkyl sulfosuccinates, e.g., the sodium sulfonate or dioctyl succinate. Non-ionic agents include condensation products of fatty acid esters, fatty alcohols, fatty acid amides, or fatty-alkyl- or alkenyl-substituted phenols with ethylene oxide, fatty esters of polyhydric alcohol ethers, e.g., sorbitan fatty acid esters, condensation products of such esters with ethylene oxide, e.g., polyoxyethylene sorbitan fatty acid esters, block copolymers of ethylene oxide and propylene oxide, acetylenic glycols such as 2,4,7,9-tetraethyl-5-decyn-4,7-diol, or ethoxylated acetylenic glycols. Examples of a cationic surface-active agent include, for instance, an aliphatic mono-, di-, or polyamine such as an acetate, naphthenate, or oleate; or oxygen-containing amine such as an amine oxide of polyoxyethylene alkylamine; an amide-linked amine prepared by the condensation of a carboxylic acid with a di- or polyamine; or a quaternary ammonium salt.

Examples of inert materials include, but are not limited to, inorganic minerals such as kaolin, phyllosilicates, carbonates, sulfates, phosphates or botanical materials such as cork, powdered corncobs, peanut hulls, rice hulls, and walnut shells.

The compositions of the present invention can be in a suitable form for direct application or as a concentrate of primary composition that requires dilution with a suitable quantity of water or other diluent before application. The insecticidal concentration will vary depending upon the nature of the particular formulation, specifically, whether it is a concentrate or to be used directly. The composition contains 1 to 98% of a solid or liquid inert carrier, and 0 to 50%, optimally 0.1 to 50% of a surfactant. These compositions will be administered at the labeled rate for the commercial product, optimally about 0.01 lb.–5.0 lb. per acre when in dry form and at about 0.01 pts.–10 pts. per acre when in liquid form.

In a further embodiment, the compositions, as well as the transformed microorganisms comprising insecticidal lipases, such as lipid acyl hydrolases, of the invention, can be treated prior to formulation to prolong the insecticidal activity when applied to the environment of a target pest as long as the pretreatment is not deleterious to the activity. Such treatment can be by chemical and/or physical means as long as the treatment does not deleteriously affect the properties of the composition(s). Examples of chemical reagents include, but are not limited to, halogenating agents; aldehydes such a formaldehyde and glutaraldehyde; anti-infectives, such as zephiran chloride; alcohols, such as isopropanol and ethanol; and histological fixatives, such as Bouin's fixative and Helly's fixative (see, for example, Humason (1967), *Animal Tissue Techniques* (W. H. Freeman and Co.).

The compositions, as well as the transformed microorganisms comprising insecticidal lipases, such as lipid acyl hydrolases, can be applied to the environment of an insect pest by, for example, spraying, atomizing, dusting, scattering, coating, or pouring, introducing into or on the soil, introducing into irrigation water, by seed treatment or general application or dusting at the time when the pest has begun to appear or before the appearance of pests as a protective measure. It is generally important to obtain good control of pests in the early stages of plant growth, as this is the time when the plant can be most severely damaged. The compositions of the invention can conveniently contain another insecticide if this is thought necessary. In an embodiment of the invention, the composition is applied directly to the soil, at a time of planting, in granular form of a composition of a carrier and dead cells of a *Bacillus* strain or transformed microorganism of the invention. Another embodiment is a granular form of a composition comprising an agrochemical such as, for example, a herbicide, insecticide, or fertilizer in an inert carrier, and dead cells of a *Bacillus* strain or transformed microorganism of the invention.

The following examples are offered by way of illustration and not by way of limitation.

EXPERIMENTAL

Example 1

Effect of Lipid Hydrolases on *Diabrotica* Larvae

Insect diets for southern corn rootworm and western corn rootworm larvae are known in the art. See, for example, Rose and McCabe (1973) *J. Econ. Entomol.* 66:393, herein incorporated by reference. Insect diet was prepared and poured onto a tray. Generally 1.5 ml of diet was dispensed into each cell with an additional 120 μl of sample preparation containing the lipase of interest applied to the diet surface. Alternatively, 120 μl of PBS buffer adjusted for ammonium sulfate concentration was applied to the control group diet.

For the screening of western corn rootworm, 25 μl of a 0.8 egg agar solution was applied to lids. Trays were allowed to dry under a hood. After drying, lids were placed on trays and stored for 3–4 days at a temperature of 26° C. Trays were then scored counting "live" versus "dead" larvae and tabulating the results. The results were expressed as a percentage of mortality. Any result over 75% was considered a positive result.

Using the methods described above, non-plant lipases were tested for insecticidal activity against the western corn rootworm.

The results of feeding non-plant lipases to *Diabrotica* larvae are shown in FIG. 1. Lipase from *Candida cylindracea* (FIG. 1), from *Rhizopus arrhizus* (Table 1A), and from porcine pancreas (Table 1B) were all capable of killing larvae and stunting growth. FIG. 1 shows western corn rootworm (WCRW) bioassay results from feeding *Candida cylindracea* lipase (as set forth in SEQ ID NO:2) to developing larvae. The dietary lipase causes a dose-dependent inhibition of larval growth as a percentage of wild-type controls.

TABLE 1

| SAMPLE | MORTALITY SCORE | COMMENT |
|---|---|---|
| A. WCRW bioassay for lipase from *Rhizopus arrhizus* | | |
| 1 | 2/21 = 9% | normal |
| 2 | 1/21 = 5% | normal |
| 3 | 0/21 = 0% | normal |
| 4 | 0/21 = 0% | normal |
| 5 | 0/21 = 0% | normal |
| 6 | 0/21 = 0% | normal |
| Diet | 0/21 = 0% | normal |
| 1 mg/ml | 19/21 = 90% | severe stunting |
| .5 mg/ml | 17/21 = 81% | severe stunting |
| .25 mg/ml | 15/21 = 71% | severe stunting |
| .125 mg/ml | 7/21 = 33% | moderate-severe stunting |
| .063 mg/ml | 6/22 = 27% | moderate-severe stunting |
| .032 mg/ml | 4/23 = 17% | moderate-severe stunting |
| Diet | 0/21 = 0% | normal |
| B. WCRW bioassay for porcine pancreatic lipase | | |
| 1 mg/ml | 9/22 = 41% | moderate-severe stunting |
| .5 mg/ml | 5/20 = 25% | moderate-severe stunting |
| .25 mg/ml | 6/21 = 29% | moderate-severe stunting |
| .125 mg/ml | 1/18 = 6% | moderate-severe stunting |
| .063 mg/ml | 0/15 = 0% | moderate-severe stunting |
| .032 mg/ml | 3/20 = 15% | moderate stunting |
| Diet | 0/21 = 0% | — |

Samples 1–6 are buffer controls (different concentration of ammonium sulfate in PBS) correspondent to lipase samples 1 mg/ml to 0.32 mg/ml. All samples are dissolved in buffer PBS.
Parameters: Acrylic Trays, 7 observations/sample at 50 μl/well, 3 WCR neonates/observation, topical application and a 5-day score.

Table 1 shows western corn rootworm (WCRW) bioassay results from feeding (A) *Rhizopus arrhizus* lipase (as set forth SEQ ID NO:6) and (B) porcine pancreatic lipase (as set forth in SEQ ID NO:4) to developing larvae. Shown are the mortality scores relative to controls and observed effects on larval growth. Both lipases cause a dose-dependent increase in larval mortality and stunting of growth.

Example 2

Transformation and Regeneration of Transgenic Plants

Immature maize embryos from greenhouse donor plants are bombarded with a plasmid comprising the DNA sequence as set forth in SEQ ID NO: 1 operably linked to a ubiquitin promoter or bombarded with a plasmid comprising the DNA sequence as set forth in SEQ ID NO:5 operably linked to a ubiquitin promoter. A selectable marker gene such as PAT (Wohlleben et al. (1988) *Gene* 70:25–37), which confers resistance to the herbicide Bialaphos, is used. Alternatively, the selectable marker gene is provided on a separate plasmid. Transformation is performed as follows. Media recipes follow below.

Preparation of Target Tissue

The ears are husked and surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5 cm target zone in preparation for bombardment.

A plasmid vector comprising the DNA sequence as set forth in SEQ ID NO:1 or the DNA sequence as set forth in SEQ ID NO:5 is made. This plasmid DNA plus plasmid DNA containing a PAT selectable marker is precipitated onto 1.1 μm (average diameter) tungsten pellets using a $CaCl_2$ precipitation procedure as follows: 100 μl prepared tungsten particles in water; 10 μl (1 μg) DNA in Tris EDTA buffer (1 μg total DNA); 100 μl 2.5 M $CaCl_2$; and, 10 μl 0.1 M spermidine.

Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.

The sample plates are bombarded at level #4 in particle gun #HE34-1 or #HE34-2. All samples receive a single shot at 650 PSI, with a total of ten aliquots taken from each tube of prepared particles/DNA.

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2–4 weeks), well-developed somatic embryos are transferred to medium for germination and transferred to the lighted culture room. Approximately 7–10 days later, developing plantlets are transferred to 272V hormone-free medium in tubes for 7–10 days until plantlets are well established. Plants are then transferred to inserts in flats (equivalent to 2.5" pot) containing potting soil and grown for 1 week in a growth chamber, subsequently grown an additional 1–2 weeks in the greenhouse, then transferred to classic 600 pots (1.6 gallon) and grown to maturity. Plants are monitored and scored for insect resistance and/or lipase activity.

Bombardment medium (560Y) comprises 4.0 g/l N6 basal salts (SIGMA C-1416), 1.0 ml/l Eriksson's Vitamin Mix (1000× SIGMA-1511), 0.5 mg/l thiamine HCl, 120.0 g/l sucrose, 1.0 mg/l 2,4-D, and 2.88 g/l L-proline (brought to volume with D-I $H_2O$ following adjustment to pH 5.8 with KOH); 2.0 g/l Gelrite (added after bringing to volume with D-I $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000× SIGMA-1511), 0.5 mg/l thiamine HCl, 30.0 g/l sucrose, and 2.0 mg/l 2,4-D (brought to volume with D-I $H_2O$ following adjustment to pH 5.8 with KOH); 3.0 g/l Gelrite (added after bringing to volume with D-I $H_2O$); and 0.85 mg/l silver nitrate and 3.0 mg/l bialaphos(both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I $H_2O$) (Murashige and Skoog (1962) *Physiol. Plant.* 15:473), 100 mg/l myo-inositol, 0.5 mg/l zeatin, 60 g/l sucrose, and 1.0 ml of 0.1 mM abscisic acid (brought to volume with polished D-I $H_2O$ after adjusting to pH 5.6); 3.0 g/l Gelrite (added after bringing to volume with D-I $H_2O$); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I $H_2O$), 0.1 g/l myo-inositol, and 40.0 g/l sucrose (brought to volume with polished D-I $H_2O$ after adjusting pH to 5.6); and 6 g/l bacto-agar (added after bringing to volume with polished D-I $H_2O$), sterilized and cooled to 60° C.

Example 3

*Agrobacterium*-Mediated Transformation

For *Agrobacterium*-mediated transformation of maize with a lipase expression cassette comprising the sequence as set forth in SEQ ID NO: 1 operably linked to a ubiquitin promoter, the method of Zhao can be employed (U.S. Pat. No. 5,981,840, and International Patent Publication No. WO 98/32326; the contents of which are hereby incorporated by reference). Briefly, immature embryos are isolated from maize and the embryos contacted with a suspension of *Agrobacterium*, where the bacteria are capable of transferring the lipase expression cassette to at least one cell of at least one of the immature embryos (step 1: the infection step). In this step the immature embryos are generally immersed in an *Agrobacterium* suspension for the initiation of inoculation. The embryos are co-cultured for a time with the *Agrobacterium* (step 2: the co-cultivation step). Generally, the immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). Generally, the immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). Generally, the immature embryos are cultured on solid medium with a selective agent resulting in the selective growth of transformed cells. The callus is then regenerated into plants (step 5: the regeneration step), and, generally, calli grown on selective medium are cultured on solid medium to regenerate the plants. Transformed plants are then grown and selected according to the methods in Example 3.

Example 4

Soybean Embryo Transformation

Soybean embryos are bombarded with a plasmid having the expression cassette comprising SEQ ID NO:1 operably linked to a ubiquitin promoter as follows. To induce somatic embryos, cotyledons, 3–5 mm in length dissected from surface-sterilized, immature seeds of the soybean cultivar A2872, are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can be maintained in 35 ml liquid media on a rotary shaker, 150 rpm, at 26° C. with florescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein et al. (1987) *Nature (London)* 327:70–73, U.S. Pat. No.4,945,050). A DuPont Biolistic PDS1000/HE instrument (helium retrofit) can be used for these transformations.

A selectable marker gene that can be used to facilitate soybean transformation is a transgene composed of the 35S promoter from Cauliflower Mosaic Virus (Odell et al. (1985) *Nature* 313:810–812), the hygromycin phosphotransferase gene from plasmid pJR225 (from *E. coli*; Gritz et al. (1983) *Gene* 25:179–188), and the 3' region of the nopaline synthase gene from the T-DNA of the Ti plasmid of *Agrobacterium tumefaciens*. The expression cassette comprising SEQ ID NO: 1 operably linked to the ubiquitin promoter can be isolated as a restriction fragment. This fragment can then be inserted into a unique restriction site of the vector carrying the marker gene.

To 50 µl of a 60 mg/ml 1 µm gold particle suspension is added (in order): 5 µl DNA (1 µg/µl), 20 µl spermidine (0.1M), and 50 µl $CaCl_2$ (2.5M). The particle preparation is then agitated for three minutes, spun in a microfuge for 10 seconds and the supernatant removed. The DNA-coated particles are then washed once in 400 µl 70% ethanol and resuspended in 40 µl of anhydrous ethanol. The DNA/particle suspension can be sonicated three times for one second each. Five microliters of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 5

Sunflower Meristem Tissue Transformation

Sunflower meristem tissues are transformed with an expression cassette comprising SEQ ID NO: 1 operably linked to a ubiquitin promoter as follows (see also European Patent Number EP 0 486233, herein incorporated by reference, and Malone-Schoneberg et al. (1994) *Plant Science* 103:199–207). Mature sunflower seed (*Helianthus annuus* L.) are dehulled using a single wheat-head thresher. Seeds are surface sterilized for 30 minutes in a 20% Clorox bleach solution with the addition of two drops of Tween 20 per 50 ml of solution. The seeds are rinsed twice with sterile distilled water.

Split embryonic axis explants are prepared by a modification of procedures described by Schrammeijer, et al. (Schrammeijer et al. (1990) *Plant Cell Rep.* 9:55–60). Seeds are imbibed in distilled water for 60 minutes following the surface sterilization procedure. The cotyledons of each seed are then broken off, producing a clean fracture at the plane of the embryonic axis. Following excision of the root tip, the explants are bisected longitudinally between the primordial leaves. The two halves are placed, cut surface up, on GBA medium consisting of Murashige and Skoog mineral elements (Murashige, et al. (1962) *Physiol. Plant.*, 15: 473–497), Shepard's vitamin additions (Shepard (1980) in *Emergent Techniques for the Genetic Improvement of Crops* (University of Minnesota Press, St. Paul, Minn.), 40 mg/l adenine sulfate, 30 g/l sucrose, 0.5 mg/l 6-benzyl-aminopurine (BAP), 0.25 mg/l indole-3-acetic acid (IAA), 0.1 mg/l gibberellic acid (GA3), pH 5.6, and 8 g/l Phytagar.

The explants are subjected to microprojectile bombardment prior to *Agrobacterium* treatment (Bidney, et al. (1992) *Plant Mol. Biol.* 18:301–313). Thirty to forty explants are placed in a circle at the center of a 60×20 mm plate for this treatment. Approximately 4.7 mg of 1.8 mm tungsten microprojectiles are resuspended in 25 ml of sterile TE buffer (10 mM Tris HCl, 1 mM EDTA, pH 8.0) and 1.5 ml aliquots are used per bombardment. Each plate is bombarded twice through a 150 mm nytex screen placed 2 cm above the samples in a PDS 1000® particle acceleration device.

Disarmed *Agrobacterium tumefaciens* strain EHA105 is used in all transformation experiments. A binary plasmid vector comprising the expression cassette that contains the lipase gene operably linked to the ubiquitin promoter is introduced into *Agrobacterium* strain EHA105 via freeze-thawing as described by Holsters, et al. (1978) *Mol. Gen. Genet.* 163:181–187. This plasmid further comprises a kanamycin selectable marker gene (i.e., nptII). Bacteria for plant transformation experiments are grown overnight (28° C. and 100 RPM continuous agitation) in liquid YEP medium (10 gm/l yeast extract, 10 gm/l Bactopeptone, and 5 gm/l NaCl, pH 7.0) with the appropriate antibiotics required for bacterial strain and binary plasmid maintenance. The suspension is used when it reaches an $OD_{600}$ of about 0.4 to 0.8. The *Agrobacterium* cells are pelleted and resuspended at a final $OD_{600}$ of 0.5 in an inoculation medium comprised of 12.5 mM MES pH 5.7, 1 gm/l $NH_4Cl$, and 0.3 gm/l $MgSO_4$.

Freshly bombarded explants are placed in an *Agrobacterium* suspension, mixed, and left undisturbed for 30 minutes. The explants are then transferred to GBA medium and co-cultivated, cut surface down, at 26° C. and 18-hour days. After three days of co-cultivation, the explants are transferred to 374B (GBA medium lacking growth regulators and a reduced sucrose level of 1%) supplemented with 250 mg/l cefotaxime and 50 mg/l kanamycin sulfate. The explants are cultured for two to five weeks on selection and then transferred to fresh 374B medium lacking kanamycin for one to two weeks of continued development. Explants with differentiating, antibiotic-resistant areas of growth that have not produced shoots suitable for excision are transferred to GBA medium containing 250 mg/l cefotaxime for a second 3-day phytohormone treatment. Leaf samples from green, kanamycin-resistant shoots are assayed for the presence of NPTII by ELISA and for the presence of transgene expression by assaying lipase and/or insecticidal activity. See, for example, U.S. Pat. No. 5,743,477 herein incorporated by reference in its entirety, and Hosteller, et al. (1991), *Methods Enzymol.*, 197:125–134.

NPTII-positive shoots are grafted to Pioneer® hybrid 6440 in vitro-grown sunflower seedling rootstock. Surface sterilized seeds are germinated in 48-0 medium (half-strength Murashige and Skoog salts, 0.5% sucrose, 0.3% gelrite, pH 5.6) and grown under conditions described for explant culture. The upper portion of the seedling is removed, a 1 cm vertical slice is made in the hypocotyl, and the transformed shoot inserted into the cut. The entire area is wrapped with parafilm to secure the shoot. Grafted plants can be transferred to soil following one week of in vitro culture. Grafts in soil are maintained under high humidity conditions followed by a slow acclimatization to the greenhouse environment. Transformed sectors of $T_0$ plants (parental generation) maturing in the greenhouse are identified by NPTII ELISA and/or by lipase activity analysis of leaf extracts while transgenic seeds harvested from NPTII-positive $T_0$ plants are identified by lipase activity analysis of small portions of dry seed cotyledon.

An alternative sunflower transformation protocol allows the recovery of transgenic progeny without the use of chemical selection pressure. Seeds are dehulled and surface-sterilized for 20 minutes in a 20% Clorox bleach solution with the addition of two to three drops of Tween 20 per 100 ml of solution, then rinsed three times with distilled water. Sterilized seeds are imbibed in the dark at 26° C. for 20 hours on filter paper moistened with water. The cotyledons and root radical are removed, and the meristem explants are cultured on 374E (GBA medium consisting of MS salts, Shepard vitamins, 40 mg/l adenine sulfate, 3% sucrose, 0.5 mg/l 6-BAP, 0.25 mg/l IAA, 0.1 mg/l GA, and 0.8% Phytagar at pH 5.6) for 24 hours under the dark. The primary leaves are removed to expose the apical meristem, around 40 explants are placed with the apical dome facing upward in a 2 cm circle in the center of 374M (GBA medium with 1.2% Phytagar), and then cultured on the medium for 24 hours in the dark.

Approximately 18.8 mg of 1.8 µm tungsten particles are resuspended in 150 µl absolute ethanol. After sonication, 8 µl of it is dropped on the center of the surface of macrocarrier. Each plate is bombarded twice with 650 psi rupture discs in the first shelf at 26 mm of Hg helium gun vacuum.

The plasmid of interest is introduced into *Agrobacterium tumefaciens* strain EHA105 via freeze thawing as described previously. The pellet of overnight-grown bacteria at 28° C. in a liquid YEP medium (10 g/l yeast extract, 10 g/l Bactopeptone, and 5 g/l NaCl, pH 7.0) in the presence of 50 µg/l kanamycin is resuspended in an inoculation medium (12.5 mM 2-mM 2-(N-morpholino) ethanesulfonic acid, MES, 1 g/l $NH_4Cl$ and 0.3 g/l $MgSO_4$ at pH 5.7) to reach a final concentration of 4.0 at OD 600. Particle-bombarded explants are transferred to GBA medium (374E), and a droplet of bacteria suspension is placed directly onto the top of the meristem. The explants are co-cultivated on the medium for 4 days, after which the explants are transferred to 374C medium (GBA with 1% sucrose and no BAP, IAA, GA3 and supplemented with 250 µg/ml cefotaxime). The plantlets are cultured on the medium for about two weeks under 16-hour-day and 26° C. incubation conditions.

Explants (around 2 cm long) from two weeks of culture in 374C medium are screened for lipase and/or insecticidal activity using assays known in the art and disclosed herein. After positive explants are identified, those shoots that fail to exhibit lipase activity are discarded, and every positive explant is subdivided into nodal explants. One nodal explant contains at least one potential node. The nodal segments are cultured on GBA medium for three to four days to promote the formation of auxiliary buds from each node. Then they are transferred to 374C medium and allowed to develop for an additional four weeks. Developing buds are separated and cultured for an additional four weeks on 374C medium. Pooled leaf samples from each newly recovered shoot are screened again by the appropriate protein activity assay. At this time, the positive shoots recovered from a single node will generally have been enriched in the transgenic sector detected in the initial assay prior to nodal culture.

Recovered shoots positive for lipase expression are grafted to Pioneer hybrid 6440 in vitro-grown sunflower seedling rootstock. The rootstocks are prepared in the following manner. Seeds are dehulled and surface-sterilized for 20 minutes in a 20% Clorox bleach solution with the addition of two to three drops of Tween 20 per 100 ml of solution, and are rinsed three times with distilled water. The sterilized seeds are germinated on the filter moistened with water for three days, then they are transferred into 48 medium (half-strength MS salt, 0.5% sucrose, 0.3% gelrite pH 5.0) and grown at 26° C. under the dark for three days, then incubated at 16-hour-day culture conditions. The upper portion of selected seedling is removed, a vertical slice is made in each hypocotyl, and a transformed shoot is inserted into a V-cut. The cut area is wrapped with parafilm. After one week of culture on the medium, grafted plants are transferred to soil. In the first two weeks, they are maintained under high humidity conditions to acclimatize to a greenhouse environment.

The article "a" and "an" are used herein to refer to one or more than one (i.e., to at least one) of the grammatical object of the article. By way of example, "an element" means one or more element.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method for creating or enhancing insect resistance in a plant, said method comprising stably introducing into said plant a DNA construct comprising a nucleotide sequence encoding a non-plant lipase operably linked to a promoter that drives expression in a plant cell, wherein said nucleotide sequence is selected from the group consisting of:
  a) the nucleotide sequence set forth in SEQ ID NO:5;
  b) a nucleotide sequence comprising at least 95% sequence identity to the sequence set forth in SEQ ID NO:5, wherein the nucleotide sequence encodes a polypeptide having insecticidal activity;
  c) a nucleotide sequence encoding a polypeptide comprising the amino acid sequence set forth in SEQ ID NO:6;
  d) a nucleotide sequence encoding a polypeptide having at least 95% sequence identity to the amino acid sequence set forth in SEQ ID NO:6, wherein said polypeptide has insecticidal activity; and
  e) the nucleotide sequence of any one of preceding items (a) through (d) wherein codon usage is optimized for expression in a plant.

2. The method of claim 1, wherein said promoter is selected from the group consisting of a constitutive promoter, an inducible promoter, and a tissue-preferred promoter.

3. The method of claim 2, wherein said tissue-preferred promoter is selected from the group consisting of a root-preferred promoter, a leaf-preferred promoter, and a seed-preferred promoter.

4. The method of claim 1, wherein the DNA construct is introduced through breeding.

5. The method of claim 1, wherein the DNA construct is introduced through transformation.

6. The method of claim 1, wherein said plant is a monocot or a dicot.

7. The method of claim 1, wherein said plant is selected from the group consisting of corn, oat, soybean, wheat, rye, rice, canola, *Brassica* sp., sorghum, sunflower, barley, millet, alfalfa, cotton, peanut, flax, safflower, palm, olive, castor bean, and coconut.

8. The method of claim 1, wherein said non-plant lipase is a polypeptide having an amino acid sequence selected from the group consisting of:
  a) the amino acid sequence set forth in SEQ ID NO:6; and,
  b) an amino acid sequence comprising at least 95% sequence identity to the sequence set forth in SEQ ID NO:6, wherein the polypeptide has insecticidal activity.

9. The method of claim 8, wherein said plant is a monocot or a dicot.

10. The method of claim 8, wherein said plant is selected from the group consisting of corn, oat, soybean, wheat, rye, rice, canola, *Brassica* sp., sorghum, sunflower, barley, millet, alfalfa, cotton, peanut, flax, safflower, palm, olive, castor bean, and coconut.

* * * * *

UNITED STATES PATENT AND TRADEMARK OFFICE
CERTIFICATE OF CORRECTION

PATENT NO. : 7,214,860 B2
APPLICATION NO. : 11/061233
DATED : May 8, 2007
INVENTOR(S) : Billy F. McCutchen It is certified that error appears in the above-identified patent and that said Letters Patent is hereby corrected as shown below:

Title Page;
(54): "NON-PLANT ENCODING" should read --NON-PLANT LIPASE ENCODING--

Column 1,

Line 1: "NON-PLANT ENCODING" should read --NON-PLANT LIPASE ENCODING--

Col. 29, lines 1-30; should be deleted and the following inserted:

TABLE 1

**A. WCRW bioassay for lipase from *Rhizopus arrhizus***

| SAMPLE | MORTALITY SCORE | COMMENT |
|---|---|---|
| 1 | 2/21=9% | normal |
| 2 | 1/21=5% | normal |
| 3 | 0/21=0% | normal |
| 4 | 0/21=0% | normal |
| 5 | 0/21=0% | normal |
| 6 | 0/21=0% | normal |
| Diet | 0/21=0% | normal |
| 1 mg/ml | 19/21=90% | severe stunting |
| .5 mg/ml | 17/21=81% | severe stunting |
| .25 mg/ml | 15/21=71% | severe stunting |
| .125 mg/ml | 7/21=33% | moderate-severe stunting |
| .063 mg/ml | 6/22=27% | moderate-severe stunting |
| .032 mg/ml | 4/23=17% | moderate-severe stunting |
| Diet | 0/21=0% | normal |

Samples 1-6 are buffer controls (different concentration of ammonium sulfate in PBS) correspondent to lipase samples 1 mg/ml to 0.32 mg/ml.
Parameters: Acrylic Trays, 7 observations/sample at 50 µl/well, 3 WCRW neonates/ observation, topical application and a 5-day score.

UNITED STATES PATENT AND TRADEMARK OFFICE
CERTIFICATE OF CORRECTION

PATENT NO. : 7,214,860 B2
APPLICATION NO. : 11/061233
DATED : May 8, 2007
INVENTOR(S) : Billy F. McCutchen It is certified that error appears in the above-identified patent and that said Letters Patent is hereby corrected as shown below:

Col. 29, lines 1-30; (cont'd)

B. WCRW bioassay for porcine pancreatic lipase

| SAMPLE | MORTALITY SCORE | COMMENT |
|---|---|---|
| 1 mg/ml | 9/22=41% | moderate-severe stunting |
| .5 mg/ml | 5/20=25% | moderate-severe stunting |
| .25 mg/ml | 6/21=29% | moderate-severe stunting |
| .125 mg/ml | 1/18=6% | moderate-severe stunting |
| .063 mg/ml | 0/15=0% | moderate-severe stunting |
| .032 mg/ml | 3/20=15% | moderate stunting |
| Diet | 0/21=0% | - |

All samples are dissolved in buffer PBS.
Parameters: Acrylic Trays, 7 observations/sample at 50 μl/well, 3 WCR neonates/observation, topical application and a 5-day score.

Signed and Sealed this

Sixteenth Day of October, 2007

JON W. DUDAS
*Director of the United States Patent and Trademark Office*